United States Patent
Law

(10) Patent No.: US 7,341,719 B1
(45) Date of Patent: Mar. 11, 2008

(54) MYOBLAST THERAPY FOR COSMETIC TREATMENT

(76) Inventor: Peter K. Law, 1770 Moriah Woods Blvd., Suite 18, Memphis, TN (US) 38117

( * ) Notice: Subject to any disclaimer, the term of this patent is extended or adjusted under 35 U.S.C. 154(b) by 906 days.

(21) Appl. No.: 09/005,034

(22) Filed: Jan. 9, 1998

Related U.S. Application Data

(60) Division of application No. 08/477,377, filed on Dec. 7, 1995, now abandoned, which is a continuation-in-part of application No. 08/354,944, filed on Dec. 13, 1994, now abandoned.

(51) Int. Cl.
*A01N 65/00* (2006.01)
*C12N 5/08* (2006.01)

(52) U.S. Cl. .................. 424/93.7; 424/93.1; 424/93.21; 435/366

(58) Field of Classification Search ............. 424/93.21, 424/93.1, 93.7; 435/366
See application file for complete search history.

(56) References Cited

U.S. PATENT DOCUMENTS

| 4,154,652 A | 5/1979 | Sawamura et al. | .......... 195/1.8 |
| 4,542,143 A | 9/1985 | Hosokawa et al. | ......... 514/356 |
| 5,139,481 A | 8/1992 | Faustman et al. | ............. 604/49 |

FOREIGN PATENT DOCUMENTS

| WO | 93/17697 | 9/1993 |
| WO | 95/14079 | 5/1995 |
| WO | 96/38544 | 12/1996 |

OTHER PUBLICATIONS

Coovert et al., Current Opinion in Neurology 7:463-470, 1994.*
DiMario et al., Neuromuscular Development and Disease, Kelly et al. ed., Raven Press, Ltd., New York, 1992.*
Hoffman, Cell Transplantation 2:49-57, 1993.*
Morgan et al., Journal of Cell Science 102:779-787, 1992.*
Morgan, "Cell and Gene Therapy in Duchenne Muscular Dystrophy", Human Gene Therapy, vol. 5, pp. 165-173, (1994).
Maltsev et al., "Embryonic Stem Cells Differentiate in vitro into Cardiomyocytes Representing Sinusnodal, Atrial and Ventricular Cell Types", Mech. Devl., vol. 44, pp. 41-50, (1993).
Koh et al., "Long-term Survival of AT-1 Cardiomyocyte Grafts in Syngeneic Myocardium", Am. J. Physiol, vol. 264, pp. 1727-1733, (1993).
Watson et al., "Working Toward Human Gene Therapy: Recombinant DNA", New York, W.H. Freeman & Co., pp. 576, (1992).
Entrikin et al., Drugs in Muscular Dystrophy of the Chicken: Corticosterone-21 Acetate; Nerve & Muscle, (1984).
C.A. Bonsett, Duchenne Muscular Dystrophy-A Rational Approach to Disease Comprehension and Therapy, Indiana Medicine, Mar., 1986.
Lee et al., "Mdx Transgenic Mouse: Restoration of Recombinant Dystrophin to the Dystrophic Muscle", Human Gene Therapy, (1993).
Rowland, "Prednisone in Duchenne Muscular Dystrophy", The Lancet, Feb. 15, 1975.
Wolfe et al., "Direct Gene Transfer into Mouse Muscle in Vivo", Science, vol. 274, pp. 1465-1468, (1990).
Folkers et al., "Treatment of Preclinical Muscular Dystrophy with Coenzyme Q", Excerpta Med. Int. Service, vol. 334, p. 158, (1974).
Law, "Reduced Regenerative Capability of Dystrophic Mouse Muscle", Exp. Neurol, vol. 60, pp. 231-243, (1978).
Young et al., "Histochemical Analysis of Newly Synthesized and Accumulated Sulfated Glycosaminoglycans During Musculogensis in the Embryonic Chic Leg.", J. Morph, vol. 201, pp. 85-103, (1989).
Jackman et al., "Catheter Recordings of Accessory Atrioventricular Pathway Activation . . . " From Cell to Bedside, pp. 491-502, (1990).
Soonpaa et al., "Formation of Nascent Intercalated Disks Between Grafted Fetal Cardiomyocytes and Host Myocardium", Science, pp. 264-298, (1994).
Huard et al., "Human Myoblast Transplantation in Immunodeficient and Immunosuppressed Mice: Evidence of Rejection Muscle Nerve", vol. 17, pp. 224-234, (1994).
Roy et al., "Antibody Formation After Myoblast Transplantation in Duchenne-Dystrophic Patients, Donor HLA Compatible", Transpl. Proc., vol. 25, pp. 995-997, (1993).
Huard et al., "Human Myoblast Transplantation Between Immunohistocompatible Donors and Recipients Produces Immune Reactions", Transpl. Proc., vol. 24, pp. 3049-3051, (1992).
Law et al., "Pathogenesis and Treatment of Hereditary Muscular Dystrophy", Kakulas BA, Mastalgia, pp. 101-118, (1990).
Law et al., "Myoblast Injection Method Regulates Cell Distribution and Fusion", Transpl. Proc. in Press.

(Continued)

*Primary Examiner*—Brenda Brumback
(74) *Attorney, Agent, or Firm*—Heller Ehrman White & McAuliffe LLP

(57) ABSTRACT

Compositions and methods of treating mammalian diseases using myoblasts, and/or their physical, genetic, chemical derivatives. Myogenic cells that are normal, or genetically or phenotypically altered are cultured and transplanted into malfunctioning and/or degenerative tissues or organs to alleviate conditions that are hereditary, degenerative, debilitating, undesirable, and/or fatal. Treatment of these conditions is not limited to the usage of mechanical, electrical or physical properties of these myogenic cells, but includes the usage of biochemicals secreted/released by the latter. The present invention discloses the use of normal myoblasts to deliver the complete normal genome to effect genetic repair, or to augment the size, or the function of tissues or organs. Certain conditions may be better served with genetically altered myogenic cells derived from gene transduction, whereas others may be better served with cytoclimes converter cells. Endogenous biochemical(s) are used to control cell fusion of myoblasts among themselves or with other cell types. An automated cell processor within a cell bank which enables the manufacture, at a single run, of unprecedented large quantities (greater than 100 billion) of normal or genotypically or phenotypically altered myogenic cells is also disclosed.

12 Claims, 26 Drawing Sheets

OTHER PUBLICATIONS

Law et al., "New Muscle Transplant Method Produces Normal Twitch Tension in Dystrophic Muscle", Nerve, vol. 2, pp. 356-363.

Law et al., "Feasibility, Safety, and Efficacy of Myoblast Transfer Therapy on Duchenne Muscular Dystrophy Boys", Cell Transplantation, vol. 1, pp. 235-244, (1992).

Law et al., "Cell Transplantation as an Experimental Treatment for Duchenne Muscular Dystrophy", Cell Transplantation, vol. 3, pp. 485-503, (1993).

Peterson, "Chimaera Mouse Study Shows absence of Disease in Genetically Dystrophic Muscle", Nature, vol. 248, pp. 561-564, (1974).

Cox et al., "Overexpression of Dystrophin in Transgenic MDX Mice Eliminates Dystrophic Symptoms Without Toxicity", Nature, vol. 364, pp. 725-729, (1993).

Milhorat, "Therapy in Muscular Dystrophy Medical Annals of the District of Columbia", vol. 23, pp. 15, (1954).

Wood, "New Therapeutic Directions in Duchenne Muscular Dystrophy Following Discovery of Dystrophin", Pathogenesis and Therapy of Duchenne and Becker, Muscular Dystrophy, Raven Press, pp. 85-99.

Annals of the District of Columbia vol. 23, pp. 15, (1954).

Van Meter, "Progressive Muscular Dystrophy", Calif. Med., vol. 79, pp. 297-299, (1990).

Nakahara, "Studies on Progressive Muscular Dystrophy", Arzneim. Forsch., vol. 15, pp. 591-595, (1965).

Drachman et al., "Prednisone in Duchenne Muscular Dystrophy", Lancet, vol. 2, pp. 1409-1412, (1974).

Coakley et al., "Mazindol in Duchenne Muscular Dystrophy", Lancet, vol. 1, No. 8578, pp. 184, (1988).

Munsat et al., "Prednisone in Duchenne Muscular Dystrophy", Lancet, vol. 1, pp. 276-277, (1975).

Siegel et al., "Failure of Corticosteroid in the Treatment of Duchenne (Pseudo-Hypertrophic) Muscular Dystrophy", I.M.J., vol. 145, pp. 32-33, (1974).

Acsadi et al., "Human Dystrophin Expression in MDX Mice After Intramuscular Injection of DNA Constructs", Nature, vol. 352, pp. 815-818, (1991).

Neumeyer et al., "Arterial Delivery of Myoblasts to Skeletal Muscle", Neurology, vol. 42, pp. 2258-2262, (1992).

Smith et al., "Genes Transferred by Retroviral Vectors into Normal and Mutant Myoblasts in Primary Cultures Are Expressed in Myotubes", Mol. & Cell. Biol., vol. 10, pp. 3268-3271, (1990).

Hyde et al., "Correction of the Ion Transport Defect in Cystic Fibrosis Transgenic Mice by Gene Therapy", Nature, vol. 362, pp. 250-255, (1993).

Hoffman et al., "Dystrophin: The Protein Product of the Duchenne Muscular Dystrophy", Locus. Cell, vol. 51, pp. 919-928, (1987).

Chen et al., "Dystrophin Cytochemistry in MDX Mouse Muscles Injected with Labeled Normal Myoblasts", Cell Transplantation, vol. 1, pp. 17-22, (1992).

Partridge et al., "Conversion of MDX Myofibers From Dystrophin-Negative to Positive by Injection of Normal Myoblasts", Nature, vol. 337, pp. 116-117, (1989).

Gussioni et al., "Normal Dystrophin Transcripts Detected in Duchenne Muscular Dystrophy Patients After Myoblast Transplantation", Nature, vol. 365, pp. 435-438, (1992).

Huard et al., "Myoblast Transplantation Produced Dystrophin-Positive Muscle Fibers in a 16-Year Old Patient with Duchenne Muscular Dystrophy", Clin. Sci., vol. 81, pp. 287-288, (1991).

Huard et al., "Human Myoblast Transplantation: Preliminary Results of 4 Cases", Muscle Nerve, vol. 15, pp. 550-560, (1992).

Law et al., "Dystrophin Production Induced by Myoblast Transfer Therapy in Duchenne Muscular Dystrophy", Lancet, vol. 336, pp. 114-115, (1990).

Law et al., "Myoblast Transfer for Duchenne Muscular Dystrophy", Acta Paediatrica, Japan, vol. 33, pp. 206-215, (1991).

Law et al., "Myoblast Transfer Therapy for Duchenne Muscular Dystrophy", Advances in Clinical Neurosciences, vol. 2, pp. 463-470, (1992).

Law et al., "Pioneering Development in Myoblast Transfer Therapy", Muscular Dystrophy Research, Elsevier Science Publishers, pp. 109-111, (1991).

Law et al., "Long-Term Improvement in Muscle Function, Structure and Biochemistry Following Myoblast Transfer is DMD", Acta Cardiomiologica, vol. 3, pp. 281-301, (1991).

Law, "Beneficial Effects of Transplanting Normal Limb-Bud Mesenchyme Into Dystrophic Mouse Muscles", Nerve and Muscle, vol. 5, pp. 619-627, (1982).

Law et al., "Histoincompatible Myoblast Injection Improves Muscle Structure and Function of Dystrophic Mice", Transplantation Proceedings, vol. XX, No. 3, Supp. 3, pp. 1144-1219, Jun. (1988).

Law, "Myoblast Transfer Improves Muscle Genetics/Structure/Function and Normalizes the Behavior and Life Span of Dystrophic Mice", Myoblast Transfer Therapy.

Law et al., "Normal Myoblast Injections Provide Genetic Treatment for Murine Dystorphy", Nerve & Muscle, vol. 11, pp. 525-533, (1988).

Barr et al., "Systemic Delivery of Recombinant Proteins by Geneticall Modified Myoblasts", Science, vol. 254, pp. 1507-1509, (1991).

Karpati et al., "Dystrophin is Expressed in MDX Skeletal Muscle Fibers After Normal Myoblast Inplantation", American journal of Pathology, vol. 135, No. 1, Jul. (1989).

\* cited by examiner

FIG.2A
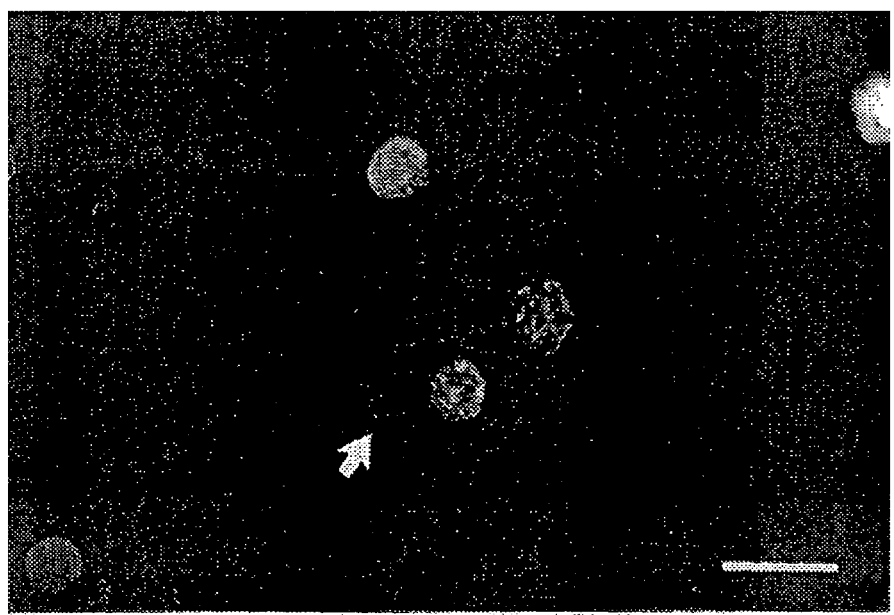
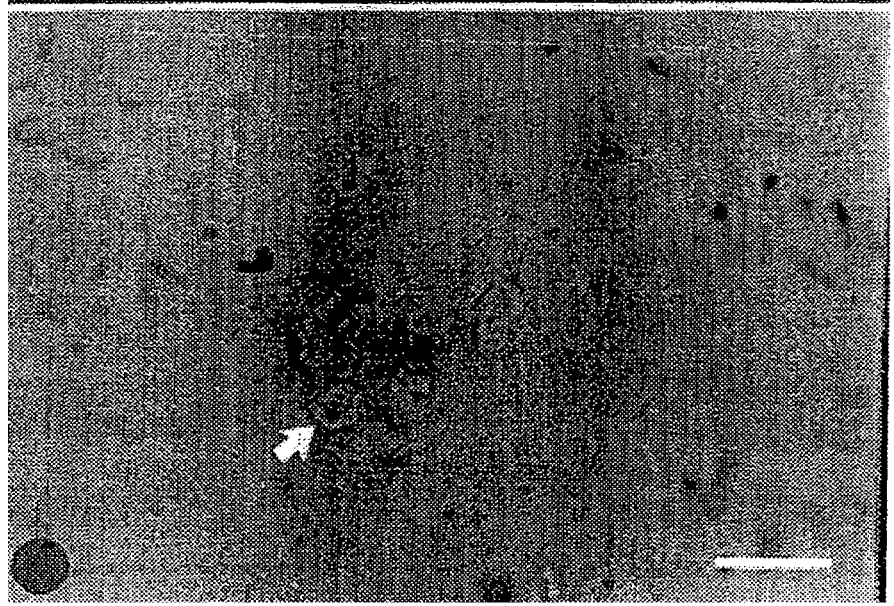
FIG.2B

FIG.8A
FIG.8B
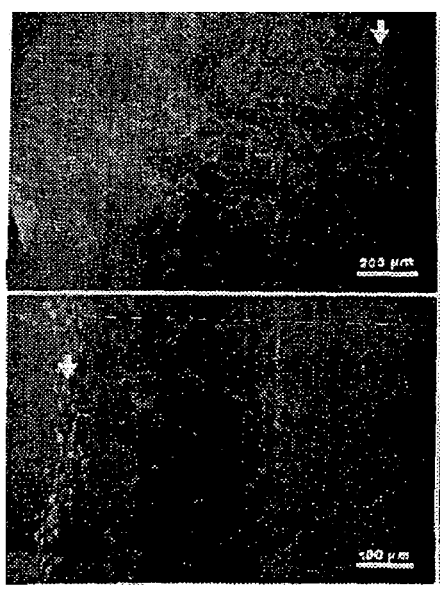
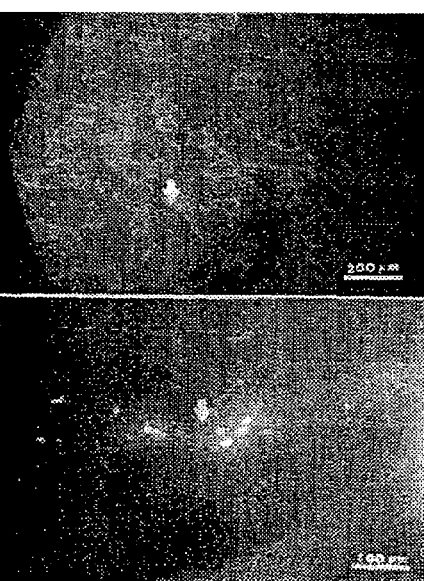
FIG.8C
FIG.8D

FIG.16E
FIG.16F
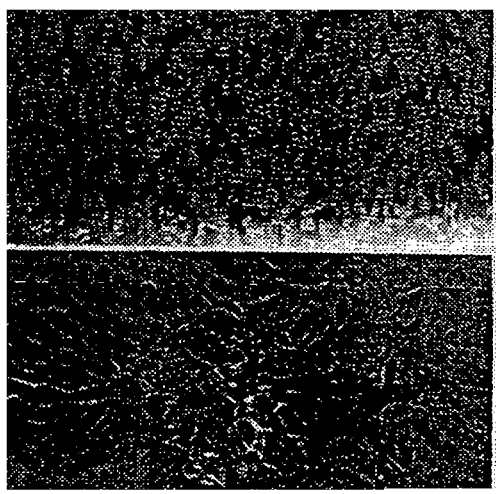
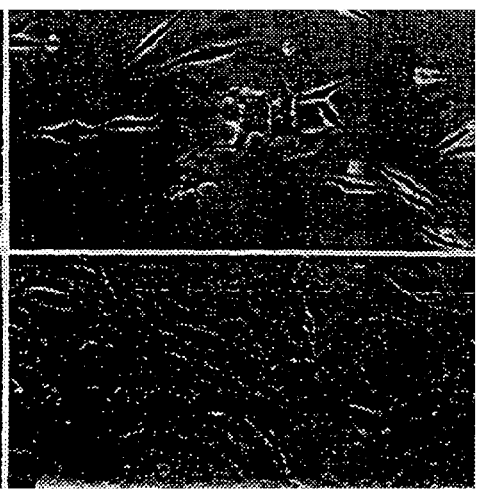
FIG.16G
FIG.16H

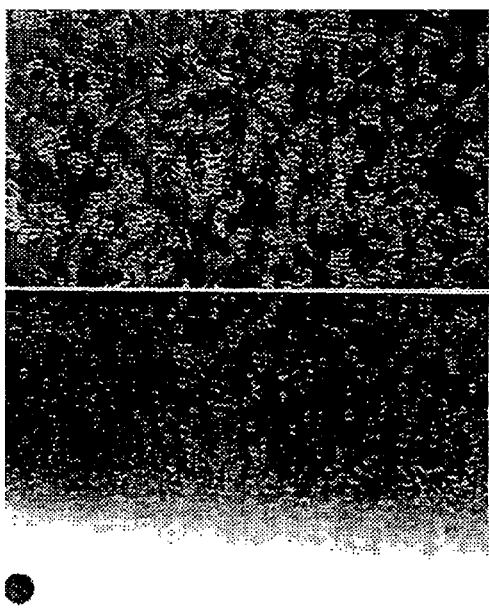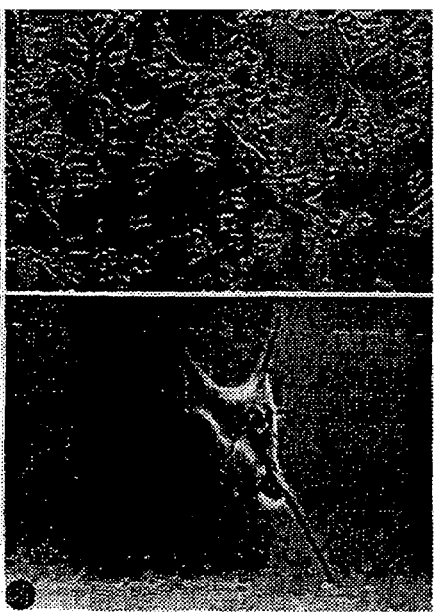
FIG.18A  FIG.18B
FIG.18C  FIG.18D

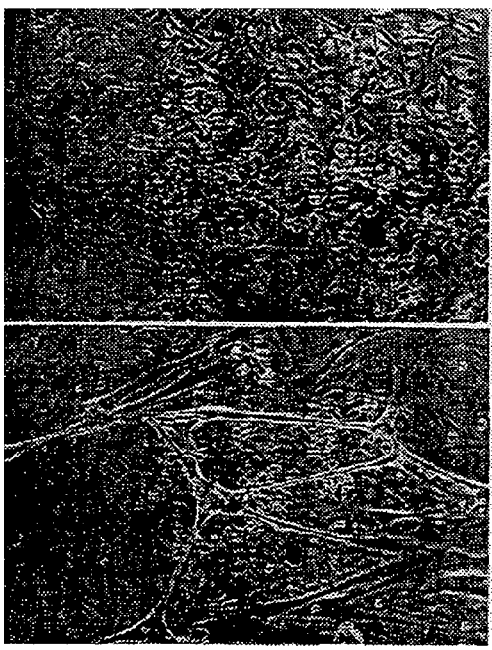
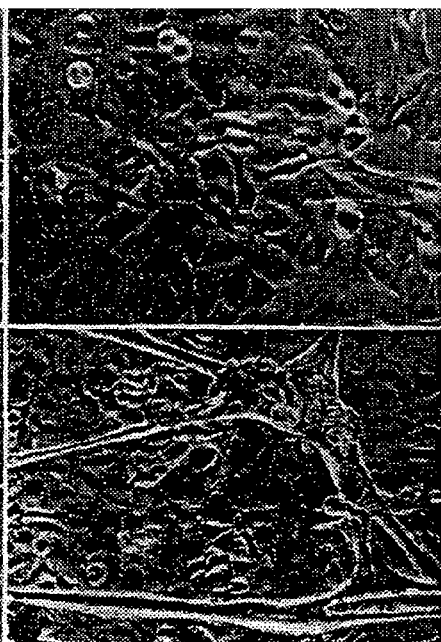
FIG.18E FIG.18F
FIG.18G FIG.18H

MYOBLAST THERAPY FOR COSMETIC TREATMENT

REFERENCE TO RELATED APPLICATION

This application is a divisional of application Ser. No. 08/477,377, filed Dec. 7, 1995, now abandoned which is a continuation-in-part of application Ser. No. 08/354,944, filed Dec. 13, 1994 now abandoned.

BACKGROUND OF THE INVENTION

1. Field of the Invention

The present invention relates to compositions and methods for treating mammalian disease conditions that are debilitating, fatal, hereditary, degenerative and/or undesirable. More specifically, the present invention relates to the transplantation of normal, or genetically transduced, or cytocline-converted myogenic cells into malfunctioning, and/or degenerative tissues or organs.

2. Description of the Prior Art

Myoblast Properties

In mammals, myoblasts are the only cell type which divide extensively, migrate, fuse naturally to form syncytia, lose their major histocompatibility Class I (MHC 1) antigens soon after fusion, and develop to occupy 50% of the body weight in humans. These combined properties render myoblasts ideal for gene transfer and somatic cell therapy (SCT). Myoblast therapy is a combined SCT and gene therapy.

Myoblast Therapy

Although the role of myoblasts/satellite cells in myogenesis and muscle regeneration dated back to the early 1960s (Konigsberg, I. R., Science, 140:1273 (1963). Mauro, A. J., Biophys. Biochem. Cytol., 9:493–495 (1961)), their use in animal therapy was not reported until 1978 (Law, P. K., Exp. Neurol., 60:231–243 1978)).

The first myoblast transfer therapy (MTT) on a Duchenne muscular dystrophy (DMD) boy on Feb. 15, 1990 marked the first clinical trial on human gene transfer. Its success was reported (Law, P. K. et al., Lancet, 336:114–115 (1990); Kolata, G. The New York Times, Sunday, (Jun. 3, 1990)). Unlike bone marrow transplant which strictly replaces genetically abnormal cells with normal ones, MTT actually inserts, through natural cell fusion, all the normal genes within the nuclei of the donor myoblasts into the dystrophic myofibers to repair them. In addition, donor myoblasts also fuse among themselves, forming genetically normal myofibers to replenish degenerated ones. Thus, full complements of normal genes are integrated, through a natural developmental process of regeneration, into the abnormal cells and into the abnormal organ.

The US Patent Office issued to this inventor a patent (U.S. Pat. No. 5,130,141) entitled "Composition for and methods of treating muscle degeneration and weakness" on Jul. 14, 1992.

In October, 1993, the Food and Drug Administration (FDA) officially began regulating somatic cell therapy (SCT) with a definition of "autologous, allogenic, or xenogeneic cells that have been propagated, expanded, selected, pharmacologically treated, or otherwise altered in biological characteristics ex vivo to be administered to humans and applicable to the prevention, treatment, cure, diagnosis, or mitigation of disease or injuries." (Federal Register, 58:53248–53251 (1993)).

MTT falls under the umbrella of SCT and myoblasts and its physical, genetic or chemical derivatives become potential biologics in the treatment of mammalian diseases.

As of May 25, 1994 the FDA has granted permission for Cell Therapy Research Foundation (CTRF) to charge $63,806 per subject. CTRF is an non-profit 501 (c) (3) research foundation founded by the inventor in 1991. Authorization by the FDA for CTRF to recover costs from subjects of these clinical trials is extremely important to establish the scientific credibility MTT and CTRF deserve, quoting the Jun. 17, 1994 edition of the Memphis Health Care News, "Permission to bill for an Investigational product is granted rarely," says FDA spokesman Monica Revelle, "Applicants must endure numerous procedures, and must have what looks like a viable product at the end of the rainbow. It's used mainly to support testing of promising technology by small companies." This statement was made in regard to research at CTRF.

At this time CTRF holds the first and only FDA-approved human clinical trial under an Investigational New Drug (IND) application on MTT. It is extremely important to realize that CTRF has been working closely with the FDA to establish criteria and policies in the approval process of this IND for genetic cell therapy. The use of viral vector mediated gene therapy on human neuromuscular diseases has not met FDA approval.

Cell Therapy with Myoblasts

The cell is the basic unit of all lives. It is that infinitely small entity which life is made of. With the immense wisdom and knowledge of the human race, we have not been able to produce a living cell from nonliving ingredients such as DNA, ions, and biochemicals.

Cell Culture is the only method known to man for the replication of cells in vitro. With proper techniques and precautions, normal or transformed cells can be cultured in sufficient quantity to repair, and to replenish degenerates and wounds.

Cell transplantation bridges the gap between in vitro and in vivo systems, and allows propagation of "new life" in degenerative tissues or organs of the living yet genetically defective or injured body.

Cell fusion transfers all the normal genes within the nucleus like delivering a repair kit to the abnormal cell. It is important to recognize that, for proper installation and future operation, the software packaged in the chromosomes needs other cell organelles as hardware to operate.

Correction of a gene defect occurs spontaneously at the cellular level after cell fusion. The natural integration, regulation and expression of the full complement of over 80,000 normal genes impart the normal phenotypes onto the heterokaryon. Protein(s) or factor(s) that were not produced by the host genome because of the genetic defect are now produced by the donor genome that is normal. Various cofactors derived from expression of the other genes corroborate to restore the normal phenotype.

Gene Therapy with Myoblasts

The use of myoblasts as gene transfer vehicles has been researched by this inventor extensively. In mammals, myoblasts are the only cell type which divide extensively, migrate, fuse naturally to form syncytia, lose MHC-1 antigens soon after fusion, and develop to occupy 50% of the body weight in humans. These combined properties render myoblasts ideal for gene transfer.

Natural transduction of normal nuclei ensures orderly replacement of dystrophin and related proteins at the cellular level in DMD. This ideal gene transfer procedure is unique to muscle. After all, only myoblasts can fuse and only muscle fibers are multinucleated in the human body. By harnessing these intrinsic properties, MTT transfers all normal genes to effect genetic repair. Since donor myoblasts also fuse among themselves to form normal fibers in MTT, the muscles benefit from the addition of genetically normal cells as well.

Myoblast Therapy is the Medicine of the Future

Health is the well-being of all body cells. In hereditary or degenerative diseases, sick cells need repairing and dead cells need replacing for health maintenance.

Cell culture is the only way to generate new, live cells that are capable of surviving, developing and functioning in the body after transplantation, replacing degenerated cells that are lost.

Myoblasts are the only cells in the body capable of natural cell fusion. The latter allows the transfer of all of the normal genes into genetically defective cells to effect phenotypic repair through complementation. MTT on DMD is the first human gene therapy demonstrated to be safe and effective. The use of MTT to transfer any other genes and their promoters/enhancers to treat other forms of diseases is underway. Myoblasts are efficient, safe and universal gene transfer vehicles, being endogenous to the body. Since a foreign gene always exerts its effect on a cell, cell therapy will always be the common pathway to health. After all, cels are what life is made of.

DMD: a Sample Disease

DMD is a hereditary, degenerative, debilitating, fatal, and undesirable mammalian disease. It is characterized by progressive muscle degeneration and loss of strength. These symptoms begin at 3 years of age or younger and continue throughout the course of the disease. Debilitating and fatal, DMD affects 1 in 3300 live male births, and is the second most common lethal hereditary disease in humans. DMD individuals are typically wheelchair-bound by age 12, and 75% die before age 20. Pneumonia usually is the immediate cause of death, with underlying respiratory muscle degeneration and failure of DMD individuals to inhale sufficient oxygen and to expel lung infections. Cardiomyopathic symptoms develop by mid-adolescence in about 10% of the DMD population. By age 18, all DMD individuals develop cardiomyopathy, but cardiac failure is seldom the primary cause of death.

Before 1950, over 80 chemicals were evaluated and 33 were reported as potentially beneficial (Milhorat, A. T., *Medical Annals of the District of Columbia*, 23:15 (1954)). None are currently being used (Wood, D. S., In: Kakulas, B. A. and Mastaglia, F. L., eds.: Pathogenesis and therapy of Duchenne and Becker muscular dystrophy. New York: Raven Press; 85–99 (1990)). Unconfirmed therapeutic benefits in DMD have been reported with vitamins, amino acids (Van Meter, J. R., *Calif. Med.*, 79:297 (1953)), ATP (Nakahara, M., *Arzneim. Forsch.*, 15:591(1965)), coenzyme Q (Folkers, K. et al., *Excerpta Med. Int. Congr. Ser.*, 334:158 (1974)), adenylosuccinic acid (Bonsett, C. A., *Indiana Medicine*, 79:236 (1986)) and growth hormone inhibitor (Coakley, J. H. et al., *Lancet*, 1(8578): 184 (1988)). Several hundred drugs have been screened (Wood, supra), with some studies showing consistent benefits from steroids (Entrikin, R. K. et al., *Muscle Nerve*, 7:130–136 (1984)).

The beneficial effects of prednisone on DMD was first reported almost 20 years ago (Drachman, D. B. et al., *Lancet*, 2:1409–1412 (1974)). The researchers reported that prednisone could delay the degenerative process and in some cases even transiently strengthen DMD muscles. The evidence substantiating prednisone is not without debate (see Munsat, T. L. and Walton, J. N., *Lancet*, 1:276–277 (1985); Rowland, L. P., *Lancet*, 1:277 (1975); and Siegel, I. M. et al., I.M.J., 145:32–33 (1974)). Although the mechanism(s) through which prednisone mediates its effect is undefined. Prednisone causes numerous side-effects, and prolonged use induces adverse reactions that by far outweigh the questionable benefits reported.

Gene manipulation and transfer are other approaches that are being used to treat hereditary and degenerative diseases. However, it will be quite some time before this type of treatment finds clinical application for DMD (Law, P. K., In: Kakulas, B. A. et al., eds.: Pathogenesis and therapy of Duchenne and Becker muscular dystrophy. New York: Raven Press, 190 (1990); and Watson, J. D. et al., Recombinant DNA. New York: W.H. Freeman and Co.; 576 (1992)). Success claimed over intramuscular DNA injections (Acsadi, G. et al., *Nature*, 352: 815–818 (1991); and Wolff, J. A. et al., *Science*, 247:1465–1468 (1990)) and arterial delivery of immature muscle cells, also known as myoblasts, to skeletal muscle (Neumeyer, A. M. et al., *Neurology*, 42:2258–2262 (1992)) is very limited and questionable. Attempt of using transfected autologous myoblasts has resulted in low efficiency and mutation in transfection (Barr, E. and Leiden, J. M., *Science*, 254: 1507–1509 (1991); Dhawan, J. et al., *Science*, 254: 1509–1512 (1991); and Smith, B. F. et al., *Mol. Cell. Biol.*, 10: 3268–3271 (1990)). Such approach will yield insufficient myogenic cells to provide for a whole body myoblast transfer therapy (MTT) to treat DMD patients (Law, supra). Clinical trials are currently underway for cystic fibrosis (CF) based on transgenic mice studies (Hyde, S. C. et al., *Nature*, 362: 250–255- (1993)). Clinical trials with gene therapy have also been attempted on severe combined immunodeficiency (SCID). Unlike CF and SCID whose genetic defects are mediated through enzymic deficiencies, the genetic defect of DMD manifested as the absence of a structural protein called dystrophin in the cell membrane rather than a regulatory protein.

Although dystrophin serves as a good genetic/biochemical marker (Hoffman, E. P. et al., *Cell*, 51: 919–928 (1987)) in the evaluation of muscle improvements, dystrophin replacement constitutes only part of the treatment process. This has already been demonstrated, among others, by the present inventor using MTT in mdx mice (Chen, M. et al., *Cell Transplantation*, 1:17–22 (1992); Karpati, G. et al., *Am. J. Pathol.*, 135: 27–32 (1989); and Patridge, T. A., et al., *Nature*, 337:176–179 (1989)) and in humans (Gussoni, E., et al., *Nature*, 356: 435–438 (1992); Huard, J. et al., *Clin. Sci.*, 81:287–288(1991); Huard, J. et al., *Muscle Nerve*, 15:550–560 (1992); Law, P. K. et al., *Lancet*, 336:114–115 (1990); Law, P. K. et al., *Acta Paediatr. Jpn.*, 33:206–215 (1991); Law, P. K. et al., *Adv. Clin. Neurosci.*, 2:463–470 (1992); Law, P. K. et al., In: Angelini, C. et al., eds. Muscular dystrophy research. New York: Elsevier Science Publishers, 109–116 (1991); and Law, P. K. et al., *Acta Cardiomiologica*, 3:281–301 (1991)). Because DMD pathology is one of muscle degeneration and weakness, structural and especially functional improvements are of primary concern. These two parameters have been extensively studied using the $dy^{2J}/dy^{2J}$ dystrophic mouse as an animal model of hereditary muscle degeneration (Law, P. K., *Exp. Neurol.*, 60:231–243 (1978); Law, P. K., *Muscle Nerve*, 5:619–627 (1982); Law, P. K. et al., *Transplant Proc.*, 20:1114–1119 (1988); Law, P. K. et al., In: Griggs, R. C.; Karpati, G., eds. Myoblast Transfer Therapy. New: Plenum Press; 75–87 (1990); Law, P. K. et al., *Muscle Nerve*, 11:525–533 (1988);

Law, P. K. et al., In: Kakulas, B. A.; Mastaglia, F. L., eds. Pathogenesis and therapy of Duchenne and Becker muscular dystrophy. New York: Raven Press; 101–118 (1990); and Law, P. K. and Yap, J. L., Muscle Nerve, 2:356–363 (1979)). These studies lead to the first MTT clinical trial or single muscle treatment (SMT) (Gussoni, E. et al., Nature, 356: 435–438 (1992); Huard, J. et al., Clin. Sci., 81:287–288 (1991); Huard, J. et al., Muscle Nerve, 15:550–560 (1992); Law, P. K. et al., Lancet, 336:114–115 (1990); Law, P. K. et al., Acta Paediatr. Jpn., 33:206–215 (1991); Law, P. K. et al., Adv. Clin. Neurosci., 2:463–470 (1992); Law, P. K. et al., In: Angelini, C. et al., eds. Muscular dystrophy research. New York: Elsevier Science Publishers: 109–116 (1991); and Law, P. K. et al., Acta Cardiomiologica 3:281–301 (1991)).

The feasibility, safety, and efficacy of MTT were assessed by this inventor in experimental lower body treatments involving 32 DMD boys aged 6–14 years of age, half of whom were non-ambulatory (Law, P. K. et al., Cell Transplantation, 2; 485–505 (1993)). Through 48 injections, 5 billion ($55.6 \times 10^6$/mL) normal myoblasts were transferred into 22 major muscles in both lower limbs in each of the subjects. Results at 9 months after MTT indicated, interalia, that (1) MTT is a safe treatment; (2) MTT improves muscle function in DMD; and (3) more than 5 billion myoblasts are necessary to strengthen both lower limbs of a DMD boy between 6 and 14 years of age.

Other Disease Conditions

Potentially every genetic disease can be benefited by MTT. Through natural cell fusion, donor myoblasts insert full complement of normal genes into genetically abnormal cells to effect repair. Promoters and enhancers of the defective gene can be supplied or activated or repressed to achieve gene transcription and translation with the release of hormone(s) or enzyme(s) from transplanted myogenic cells. Likewise, structural protein(s) can be produced to prevent or to alleviate disease conditions.

Alternatively transduced myoblasts can be used. The procedure consists of a) obtaining a muscle biopsy from the patient, b) transfecting a "seed" amount of satellite cells with the normal gene, c) confirming the myogenicity of the transfected cells, d) proliferating the transfected myoblasts to an amount enough to produce beneficial effect and e) administering the myoblasts into the patient.

Retroviral vectors have been used to transfer genes into rat and dog myoblasts in primary cultures under conditions that permit the transfected myoblasts to differentiate into myotubes expressing the transferred genes (Smith, B. F. et al., Mol. Cell Biol., 10:3268–3271 (1990)). Furthermore, mice injected with murine myoblasts that are transfected with human growth hormone (hGH) show significant levels of hGH in both muscle and serum that are stable for 3 months (Dhawan, J. et al., Science, 254:1509–1512 (1991); Barr E. and J. M. Leiden, Science, 254:1507–1509 (1991)).

The transduced myoblast transfer was inspired by a similar approach on adenosine deaminase (ADA) deficiency. In the latter situation, T cells from the patient were transfected with functional ADA genes and returned to the patient after expansion in the number of the transfected cells through cell culture (Culver, K. W. et al., Transpl. Proc., 23:170–171 (1991)).

Similar approach has already been tested in animals using genetically transduced myoblasts to treat hemophilia B (Yao, S. N. et al., Gene Therapy, 1:99–107 (1994)), cardiomyopathy (Marelli, D., Cell Transplantation, 1:383–390 (1992); Koh, G. Y. et al., J. Clin. Inves., 92:1548–1554 (1993)), anemia (Hamamori, Y. et al., Human Gene Therapy, 5:1349–1356 (1994)). Undoubtedly, there will be many hereditary diseases to which myoblast therapy will apply.

Although differentiated, myoblasts are nonetheless embryonic cells that are capable of de-differentiated or even converted. Thus, myoblasts have recently been shown to be converted into osteoblasts with bone morphogenetic protein-2 (Katagiri, T. et al., J. Cell Biol., 127:1755–1766 (1994)). This study demonstrates that cytocline-converted myoblasts can be administered to patients with bone/cartilage degenerative diseases. Alternatively, it has been demonstrated that mouse dermal fibroblasts can be converted to a myogenic lineage (Gibson, A. J. et al, J. Cell Sci., 108:207–214 (1995)).

The implicated usage of myoblast transfer therapy to treat cancer and type II diabetes mellitus is described below.

Why Myoblast Therapy

In hereditary or degenerative diseases, gene defects cause cells to degenerate and die with time. An effective treatment must not only repair degenerating cells, but replenish dead cells as well. This can best be achieved by the transplantation of genetically normal cells, or somatic cell therapy. The advent of molecular genetics favors single gene manipulation which is currently being explored to treat genetic diseases. Like pharmaceuticals, single gene manipulation cannot replenish lost cells. Further, there is very limited evidence that these approaches can repair degenerating cells.

In U.S. Pat. No. 5,130,141, this inventor disclosed for the first time compositions and methods for treating muscle degeneration and weakness. A composition comprised of genetically normal myoblasts from a donor was injected into one or more of the muscles of a host having a hereditary neuromuscular disorder. Muscle structure and function were greatly improved with the injection, thereby preventing or reducing muscle weakness which is a primary cause of crippling and respiratory failure in hereditary muscular dystrophies. This transplantation of genetically normal muscle cells into the diseased muscles of patients with hereditary muscular dystrophy is known as MTT.

MTT differs significantly from the conventional single gene transfer format in several respects. In this latter gene therapy, single copies of the down-sized dystrophin gene are transduced as viral conjugates into the mature dystrophic myofibers in which many proteins, both structural and regulatory, are lost previously. Multiple gene insertion is necessary to replace these lost proteins (FIG. 1). More gene insertion is needed to produce the cofactors to regulate and to express these lost proteins in order to repair the degenerating cell.

SUMMARY OF THE INVENTION

The demonstration of preliminary feasibility, safety, and efficacy (Law et. al., Cell Transplantation, 2:485 (1993)) of myoblast transfer therapy MTT prompted this inventor to initiate a whole body trial (WBT) injecting 25 billion myoblasts into each of 64 Duchenne muscular dystrophy (DMD) boys and a boy with infantile facioscapulohumeral dystrophy (IFSH). The randomized double-blind clinical trial protocol, approved by the FDA (IND Phase II) and the Essex IRB involves two MTT procedures separated by 3 to 9 months. Each procedure delivers 200 injections or 12.5 billion myoblasts, to either 28 muscles in the upper body (UBT) or to 36 muscles in the lower body (LBT). Injected muscles include those in the neck, shoulder, back, chest, abdomen, arms, hips, and legs. Subjects take oral cyclosporine for 3 months after each MTT. One IFSH and 10 DMD boys have received WBT and 20 more DMD boys have received UBT or LBT in the past 17 months with no adverse reaction. These preliminary results indicate that the WBT is feasible and safe. While blinding will continue until the end of the study as to which side of the biceps brachii or quadriceps received myoblasts or placebo, five subjects have demonstrated immunocytochemical evidence of dystrophin in one of these muscle biopsies 3 to 9 months after MTT. The contralateral muscle biopsies show no dystrophin. The pulmonary function (FVC) either shows no deterioration, or has improved by 15 to 25% in over 80% of the subjects 3 to 6 month after MTT. About 50% of the subjects report behavioral improvement in running, balancing, climbing stairs and playing ball. One 14 yr-old DMD subject has stayed active without the need of a wheelchair after MTT (Law, P. K. et al., *Amer Soc Neural Transpl Abst., p.* 27 (1995); Law, P. K. et al., *J. Cellular Biochem. Supp,* 21A:367, (1995)).

This demonstration of feasibility and safety in administering 30 billion myoblasts into a human subject provides the pivotal evidence that myoblasts can be used as a biologic to treat human diseases. The demonstration of the dosage effectiveness further confirms the idea that myoblast therapy can be used to treat a whole variety of mammalian diseases be it a hereditary, degenerative, debilitating, fatal, or undesirable disease condition.

The present invention provides compositions and methods for repairing degenerating cells and replenishing lost cells in patients with hereditary or degenerative diseases, in particular those characterized by muscle malfunction, degeneration and weakness. In practicing the present invention, any myogenic cell may be used, regardless of whether it is of skeletal, smooth, or cardiac in origin. Transferred cell types include myoblasts, myotubes and/or young muscle fibers. The myogenic cells may be primary-cultured or cloned from muscle biopsies of normal donors. They may also be cytocline converted or genetically transduced myogenic cells. Typically, the parents, siblings, or friends of the dystrophic patient are the donors. In addition, it is contemplated that the establishment of superior cell lines of myoblasts, whether from humans or animals, will provide a ready access of healthy donor cells for patients who do not otherwise have a suitable donor (FIGS. 2 to 5, also Law, P. K., *Myoblast Transfer,* Landes, Austin, (1994)). It is further contemplated that the cell transplantation procedure will augment size, shape, appearance or function, and/or alleviate the disease conditions.

The present invention provides a method for controlling, initiating, or facilitating cell fusion once the myoblasts are injected into one or more of the muscles of a patient with the degenerative disease. By artificially increasing the concentration of the large chondroitin-6-sulfate proteoglycan (LC6SP) over the patient's endogenous level, fusion of the transferred donor myoblasts among themselves or with other cell types can be enhanced and controlled. (Law, P. K., *Myoblast Transfer Landes, Austin* (1994)).

It is yet another object of the invention to improve the fusion rate between the host and donor cells. To this end, various injection methods were tested and compared including injecting diagonally through the myofibers, perpendicular to the myofiber surface, parallel to the myofibers, and at a single site into the muscle. The goal is to achieve maximum cell fusion with the least number of injections (FIGS. 6 to 8, also Law, P. K., *Myoblast Transfer,* Landes Austin, (1994)).

In a further embodiment, the technologies of in vitro fertilization and blastomere recombination can be used on known Duchenne carriers to increase their chances of having normal children (FIGS. 9 to 13; also Law, P. K., *Myoblast Transfer,* Landes, Austin, (1994)).

It is yet another object of the present invention to provide an automated cell processor, a highly efficient means for producing mass quantities (over 100 billion in one run) of viable, sterile, genetically normal as well as functional myogenic cells whether genetically transduced or cytocline-converted. The cell processor has an intake system which will hold biopsies of various human tissues. The cell processor's computer will be programmed to process tissue(s), and will control time, space, proportions of culture constituents and apparatus functions. Cell conditions can be monitored at any time during the process. The output system provides a supply of cells suitable for transfer in cell therapy or for shipment (FIGS. 14 to 15).

It is yet another embodiment in which myoblasts, and/or their physical, genetic, chemical derivatives, are used to treat cancer. FIGS. 16 to 18 illustrate melanoma cancer cell death upon exposure to myoblasts in fusion medium. According to Cancer Prevention and Control edited by Greenwald, P., Kramer, B. S., and Weed, D. L. (Marcel Dekker, Inc. New York, 1995), skeletal muscles appear to be devoid of cancer, though malignant tumor and metastases are found in every other organ. The very few cases of sarcoma reported are rare exceptions.

The recent immunocytochemical demonstration of dystrophin in DMD muscles 9 months after MTT indicated long term correction of genetic defect(s) can result from myoblast therapy (FIG. 19). This principle can apply to treat malfunctional insulin resistant muscles in Type II diabetes mellitus. As a universal gene transfer vehicle, donor myoblasts insert the whole normal genome and this can repair any malfunction of skeletal muscle cells, rendering them insulin sensitive (FIG. 20).

Additional features and advantages are described in and will be apparent from the detailed description of the presently preferred embodiments and from the drawings. Further, all references described herein are incorporated by reference.

BRIEF DESCRIPTION OF THE DRAWINGS

FIG. 2 illustrates MHC-negative myoblasts and MHC-positive myoblasts. (A) represents human myoblasts assayed with anti-MHC class I antibodies and viewed under fluorescent microscopy. The arrow indicates the MHC-negative myoblast. (B) is of the same slide viewed under a regular light microscope. The arrow indicates the MHC-negative myoblast. Bar=20 um.

FIG. 8 illustrates distributions of donor myoblasts labeled with FG in host muscle. Even distribution of donor myoblasts can be achieved with oblique myoblast injection (A,B), or donor nuclei may appear in patches (C,D, white arrows) which gradually show more abnormal nuclei and debris. (C) represents a transverse injection and (D) a longitudinal injection.

FIG. 18 illustrates myoblasts and melanoma cells co-cultured in myoblast growth medium for 4 days and then in myoblast fusion medium. (A, C, E, G) low magnification; (B, D, F, H) high magnification. (A, B) Myoblasts and melanoma cells (1:1 concentration ratio) after 5 days in myoblast fusion medium. Many melanoma cells have become spherical and detached from the surface and are not surviving in this medium. Myoblasts remain healthy and are beginning to fuse. (C, D) Myoblasts and melanoma cells (1:1 concentration ratio) after 10 days in myoblast fusion medium show numerous dying cells. Only a few can survive in this medium for this long, and they are detached and dying (D). (E, F) Myoblasts and melanoma cells (1:1 concentration ratio) after 19 days in myoblast fusion media. The surviving myobalasts retain their spindle shape and align with each other. Melanoma cells have become spherical and detached. (G, H) Myoblasts and melanoma cells (3:1 concentration ratio) after 19 days in myoblast fusion medium. Myoblasts have begun to fuse, forming myotubes.

DETAILED DESCRIPTION OF THE PREFERRED EMBODIMENTS

Figure 1:
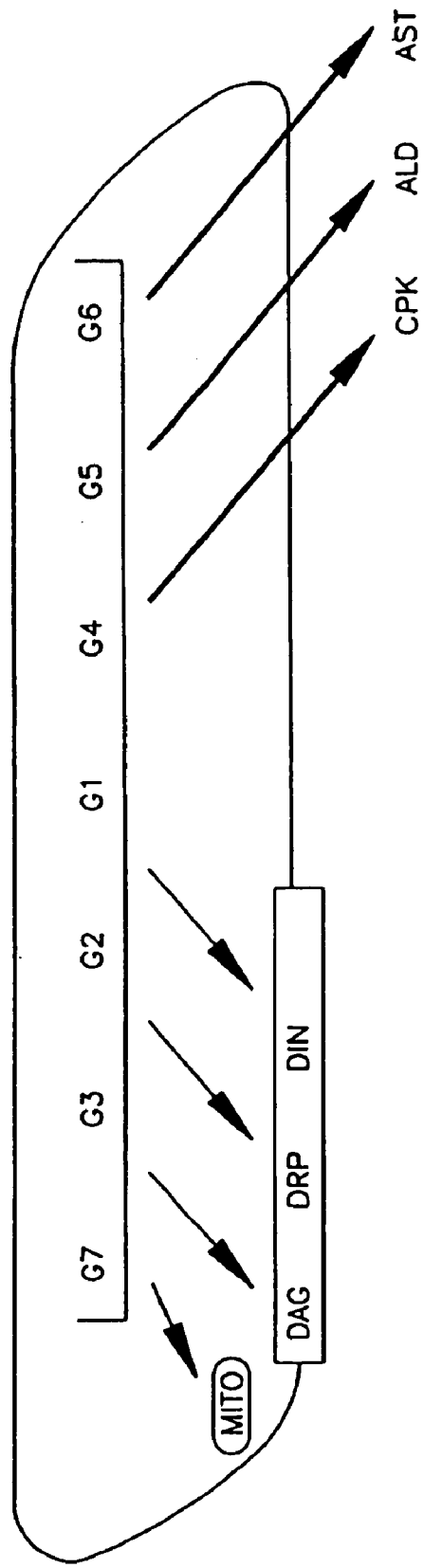
FIG. 1 is a diagram of some of the known protein defects in DMD muscle cells that differ from normal muscle cells. These include membrane structural proteins that are decreased or absent in DMD such as dystrophin (DIN), dystrophin-related-protein (DRP) and dystrophin-associated-glycoproteins (DAG), enzymes elevated in serum levels of DMD patients such as creatinine phosphokinase (CPK), aldolase (ALD) and aspartate transaminase (AST), and mitochondrial (Mito) protein differences. Although these protein defects are caused primarily or secondarily by the dystrophin gene defect, their correction will require multiple gene (G1 to G7) transfer.

The compositions and methods described herein will be illustrated for the treatment of individuals having hereditary neuromuscular diseases. However, it is contemplated that other hosts and other disease states may be treated with the inventive compositions and methods.

A. Controlled Cell Fusion

Myoblasts have the unique ability to fuse with other cells. With the use of normal myoblasts, a full complement of normal genes can be introduced into any genetically abnormal cells through cell fusion. For example, the genetically abnormal cell could be a liver cell, heart muscle cell, or even a brain cell. The idea is to introduce a full complement of normal genes into abnormal cells and, therefore, treat the genetic disease at the gene level and not at the hormonal or biochemical level.

For treating genetic diseases that involve structural protein abnormalities rather than regulatory protein abnormalities, it would be useful to control, initiate or facilitate cell fusion once myoblasts were injected into the body. It is known that myoblasts fuse readily at low serum concentrations in culture. The process is more complex in the in vivo situation. As the myoblasts are injected intramuscularly into the extracellular matrix (ECM), injection trauma causes the release of basic fibroblast growth factor (bFGF) and large chondroitin-6-sulfate proteoglycan (LC6SP) (Young, H. E., et al., *J. Morph.*, 201:85–103. (1989)). These latter growth factors stimulate myoblasts proliferation. Unfortunately, they also stimulate the proliferation of fibroblasts that are already present in increased amounts in the dystrophic muscle. It is, therefore, necessary to inject as pure as possible fractions of myoblasts in MTT without contaminating fibroblasts.

Controlled cell fusion can be achieved by artificially increasing the local concentration of LC6SP over the endogenous level at the transfer site. In muscles, this is achieved by including approximately 5 μM of LC6SP in the transfer medium. In addition, insulin facilitates the developmental process in vitro, and may result in the formation of myotubes soon after myoblast injections. The use of LC6SP (ranging from approximately 5 μM to about 5 mM) in the transfer medium will likely lead to greater MTT success.

B. Myoblasts: the Universal Gene Transfer Vehicles

Whereas MTT results in the formation of genetic mosaicism with gene transfer occurring in vivo, the production of heterokaryons in vitro has immense medical application. This can be achieved by controlled cell fusion with myoblasts.

This research relates to the in culturo transfer of the normal nuclei with all of their normal genes from donor myoblasts into the genetically normal and/or abnormal cells, e.g. the cardiomyocytes. This development is especially important considering that cardiomyopathic symptoms develop in mid-adolescence in about 10% of the DMD population. By age 18, all DMD individuals develop cardiomyopathy. Undoubtedly, the ability to replenish degenerated and degenerating cardiomyocytes will have an immense impact on heart diseases even in the normal population where there is a great shortage of hearts for transplantation.

Normal cardiomyocytes have a very limited ability to proliferate in vivo or in vitro. The heart muscles damaged in heart attacks or in hereditary cardiomyopathy cannot repair themselves through regeneration. By integrating the skeletal muscle cell characteristic, mitosis, heterkaryotic cardiomyocytes will be able to proliferate in vitro.

Controlled cell fusion between normal myoblasts and normal cardiomyocytes may result in heterokaryons exhibiting the characteristics of both parental myogenic cell types. Clones can be selected based on their abilities to undergo mitosis in vitro to develop desmosomes, gap junctions, and to contract strongly in synchrony after cell transplantation.

These genetically superior cells can then be delivered through catheter pathways of the type described by Jackman W M, et al. (In: Zipes D P, and Jalife J, eds. *Cardiac electrophysiology. From Cell to Bedside*. Philadelphia: WB Saunders Company, 491–502, (1990)) after mapping of the injured sites. With the ability to grow large quantity of these cardiomyocytes, the correction of structural, electrical and contractile abnormalities in cardiomyopathy can be tested first in dystrophic, cardiomyopathic hamsters and then in humans.

The genetic transfer of the mitotic property of myoblasts onto cardiomyocytes with in vitro controlled cell fusion enables the resulting heterokaryotic cardiomyocytes to multiply, yielding enough numbers of cells for the cell transplant to be effective.

Recently, it was reported that fetal mouse cardiomyocytes grafted into the myocardium of syngeneic hosts formed nascent intercalated disks between host and donor cells (Soonpaa M H, et al., *Science*, 264:98-(1994)). The use of fetal cells for cell transplant has and will continue to raise ethical questions. The fact still remains that fetal cells will not produce enough cardiomyocytes to mend a myocardial infarct. The bioengineering of mitotic cardiomyocytes using myoblasts provides a solution to the problem in view of reported studies that recombinant genes introduced into cardiomyocytes are expressed for at least 6 months, and appear to be regulated normally by humoral signals.

Whereas myoblast transfer into the dystrophic myocardium followed by in vivo controlled cell fusion may provide a structural impediment at the infarct, it remains to be shown that the myoblasts will integrate well with the cardiomyocytes, considering that the pumping action of the heart will disaggregate the developing cells from the host myocardium.

C. Cosmetic Usage

In a broader sense, the cell therapy concept can significantly contribute to the field of plastic surgery. With cell therapy, implantation of silicone could be avoided. The use of myoblasts and/or fat cells could be used in a much more natural way to replace silicone injections for facial, breast and hip augmentation. Modified adipose tissue involving mixing and/or hybridization of myoblasts and fat cells can be used to control size, shape and consistency of body parts. Since muscle cells do not break down as easily as fat cells, good results may be long-lasting. Today, body builders are in search of increasing muscle mass and function at the right places. The use of myoblast transfer to boost muscle mass is a natural solution.

D. Superior Cell Lines

The establishment of superior cell lines of myoblasts is a high-risk challenge, but its benefits are numerous. These cell lines should be highly myogenic, nontumorigenic, nonantigenic, and will develop very strong muscles.

A unique property of myoblasts is their loss of major histocompatibility complex class I (MHC-I) surface antigens soon after they fuse. This has important implications in the usage of an immunosuppressant after myoblast transfer therapy. (See Huard J, et al., *Muscle Nerve*, 17:224–34 (1994); Roy R, et al., *Transpl Proc*, 25:995–7 (1993); and Huard J, et al. *Transpl Proc*, 24:3049–51 (1992)). The immunosuppression period depends on how soon the myoblasts lose their MHC-I antigens after MTT. Even more ideal is the establishment of a myoblast cell line in which MHC-I antigens are absent, thereby allowing MTT without immunosuppression.

In our study, human myoblasts were cultured from normal muscle biopsies in accordance with the methods disclosed in Law, P. K., et al., *Cell Transplantation*, 1:235 (1992) and Law, P. K., et al., *Cell Transplantation*, 2:485 (1993). The MHC-I antigens expressed on the myoblasts were demonstrated with fluorescent immunoassay. Cell cycle synchronization of myoblasts was carried out by adding colchicin in the growth medium and incubating for 48 hours. The myoblast preparations used in the experiment were 98% pure as assessed by immunostaining with the monoclonal antibody (MAb) anti-Leu-19.

Myoblasts were incubated with anti-MHC-I MAb (mouse 1:25 dilution, Silenus Lab, Australia) at room temperature. After washing, the myoblasts were incubated with FITC conjugated anti-mouse-IgG (Sigma) for 45 minutes and examined under fluorescence microscope with wide band ultraviolet (UV) excitation filter. Cytofluorometry was performed with a Becton-Dickinson cell sorter operated at 488 mM. Myoblast control was carried out by omitting the first antibodies in the immunoassay as the background of autofluorescence.

Figure 3A:
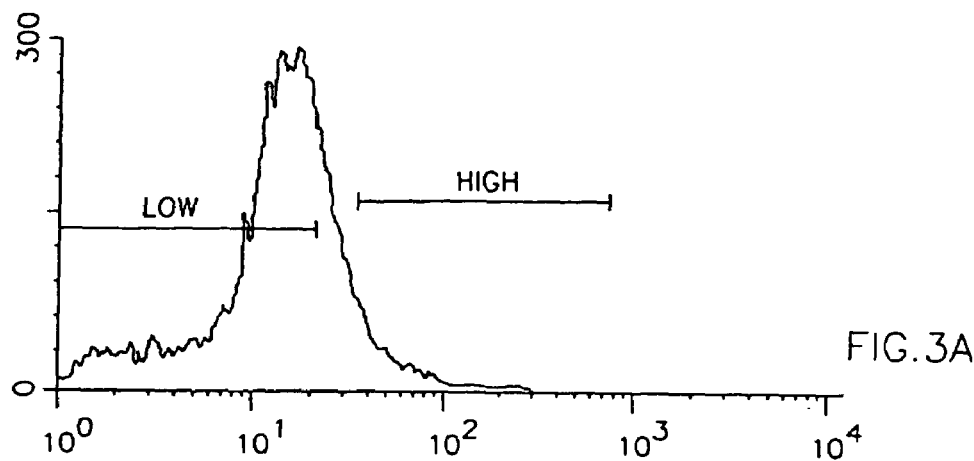
FIG. 3 illustrates an analysis of myoblasts by cytofluorometry. Control: myoblasts reacted without anti-MHC class I antibodies. Samples: myoblasts reacted with anti-MHC class I antibodies.
Figure 3B:
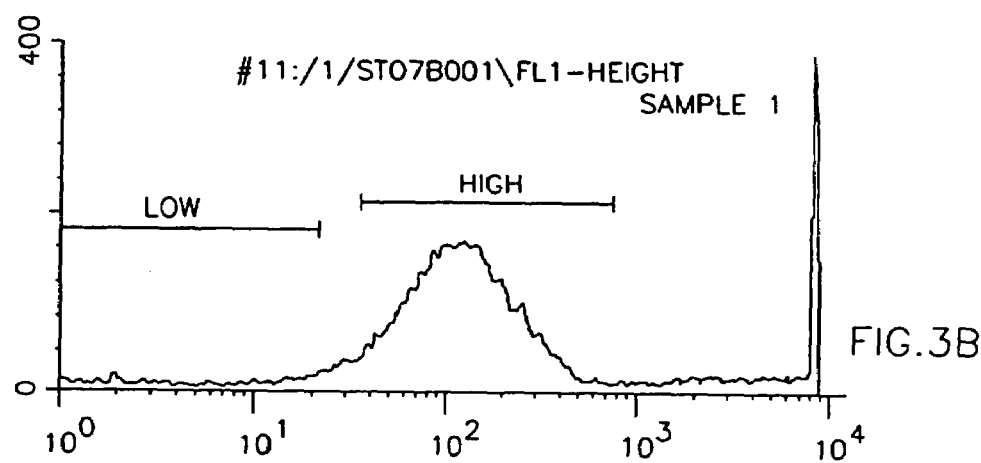
Figure 3C:
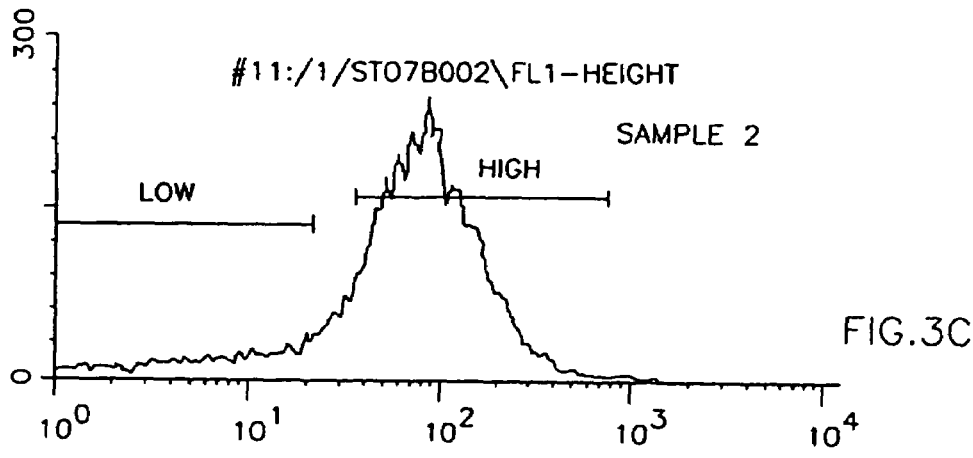
Figure 4:
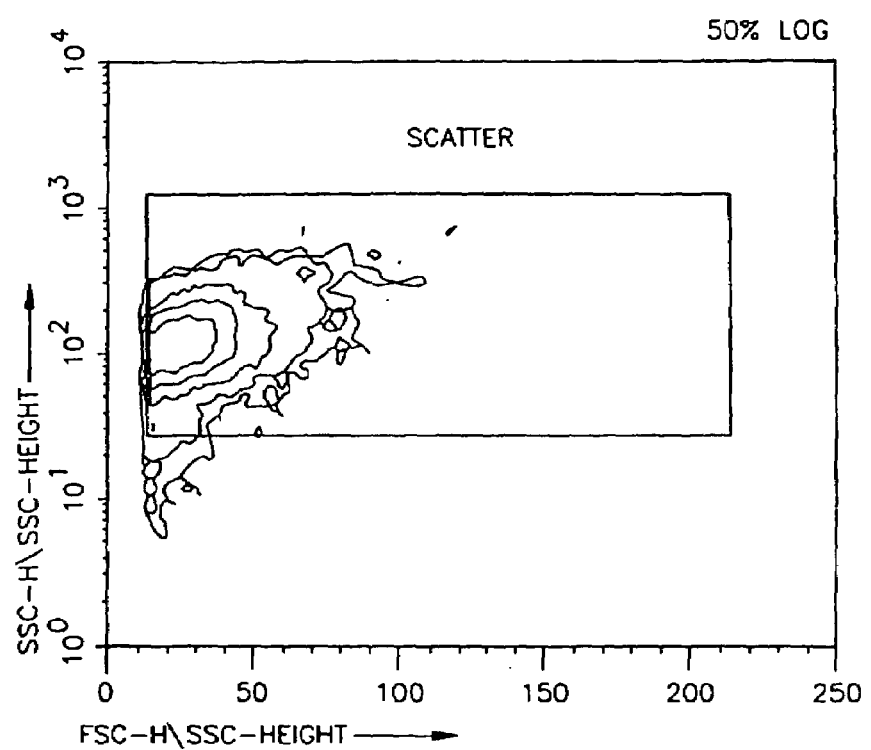
FIG. 4 is a scatter diagram of the separation of the myoblasts that were negative for MHC-I antigen expression by cytofluorometry.

91.7% of the myoblasts reacted with MHC-I MAb. The reactions ranged from strong to weak. The remaining 8.3% of the myoblasts were negative for MHC-I antigen expression. FIG. 2 illustrates both MHC-negative myoblasts and MHC-positive myoblasts. The MHC-negative myoblasts were successfully separated by cytofluorometry, which is illustrated in FIGS. 3,4. Both groups of myoblasts were then cultured for three weeks without significant difference in proliferation.

Figures 5A, 5B:
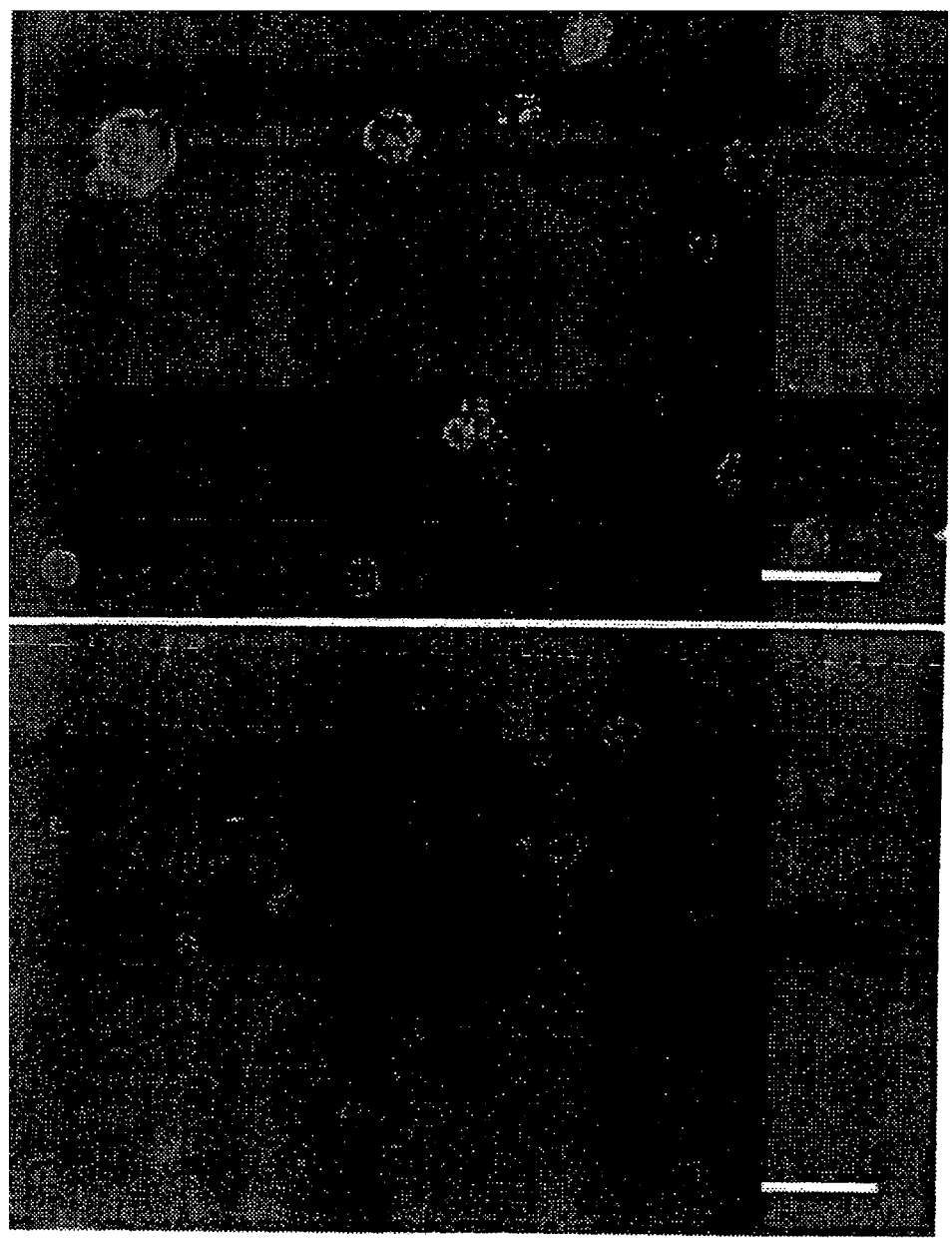
FIG. 5 illustrates fluorescent intensities of two groups of myoblasts after separation by cytofluorometry. (A) represents MHC-positive myoblasts. (B) represents MHC-negative or weakly expressed myoblasts. (A) and (B) are of the same magnification and the pictures were similarly processed. Bar=30 um.

The lack of MHC-I antigens on these myoblasts may enhance survival of these myoblasts in recipients after MTT. FIG. 5 illustrates the fluorescent intensities of both MHC-positive myoblasts and MHC-negative or weakly expressed myoblasts after separation by cytofluorometry.

The immunosuppressant, cyclosporine, has many side effects and by suppressing the immune system, allows infection to prevail. Myoblasts without MHC-I antigen expression may contribute to a new cell line more capable of surviving in the host than the regular myoblasts. This superior cell line will eliminate the need to use the immunosuppressant, and will provide a ready access for patients who do not have a donor.

These superior cell lines have to be derived from clones of primary myoblast cultures because they are selected for their unique properties. Unfortunately, it has been shown that all clones of myoblasts eventually produce tumors if allowed to proliferate excessively. Thus, these cell lines should not be allowed to proliferate over 30 generations.

E. Myoblast Injection Methods

Figure 6:
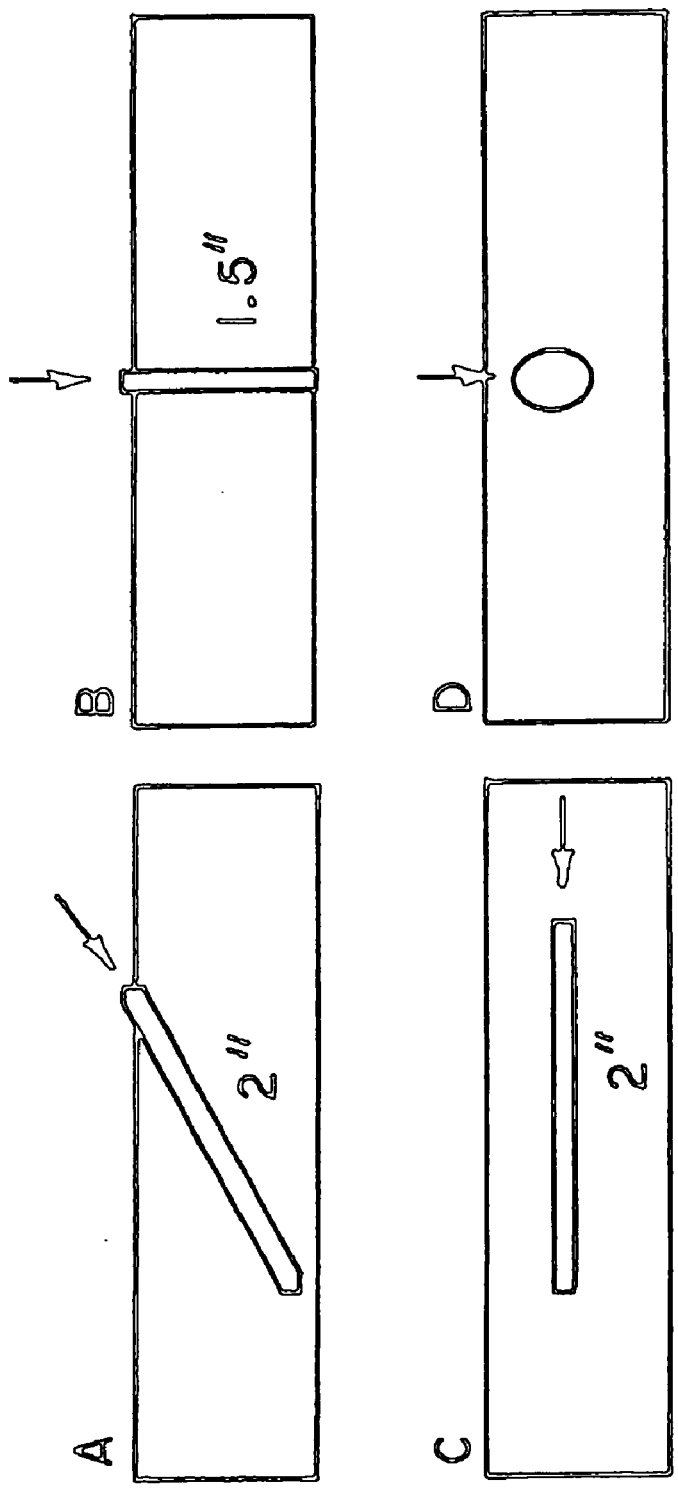
FIG. 6 illustrates the angle of injection that determines myoblast distribution. (A) Oblique myoblast injection delivers donor myoblasts to the greatest number and area of recipient muscle fibers with the least leakage, resulting in the formation of the most mosaic fibers. (B) Transverse injection delivers donor myoblasts to a large number of fibers, but covers a smaller area and is more likely to result in leakage from the injection. (C) Longitudinal injection results in donor myoblasts fusing with each other, with fewer mosaic fibers being formed. (D) Focal injection results in only a small area of a few recipient muscle fibers being injected with donor myoblasts.

Aside from donor cell survival in an immunologically hostile host, cell fusion is the key to strengthening dystrophic muscles with MTT. To improve the fusion rate between host and donor cells, various injection methods aimed at wide dissemination of donor myoblasts were tested and compared. These included injecting diagonally through the myofibers, perpendicular to the myofiber surface, parallel to the myofibers, and at a single site into the muscle. FIG. 6 illustrates myoblast distribution as a function of the angle of the injection. The goal was to achieve maximum cell fusion with the least number of injections.

Fluoro-gold (FG, 0.01%) labeled human or mouse (C57BL/6J-gpi-lc/c) myoblasts (0.05 ml of a $10^5$ cells/ml solution) were injected into the gastrocnemius muscles of twenty normal 3-month old normal mice (C57BL/6J-gpi-lb/b). Host mice were immunosuppressed with a daily subcutaneous injection of cyclosporine at 50 mg/kg body weight. Groups of mice were sacrificed on day 7, 14, 24, 34, and 44 after cell injection. Transverse sections of injected muscles were examined with fluorescence microscopy. The cell fusion rates were estimated by calculating the percentage of host muscle fibers bearing donor nuclei out of the total number of muscle fibers in the area of donor cell covered.

Figures 7A, 7B:
FIG. 7 illustrates donor myoblast nuclei labeled with fluoro-gold (FG), and are present in host muscle at seven days after MTT. (A) Mosaic myofiber with donor and recipient nuclei (black arrow) and donor myotube with donor myonuclei (white arrow). (B) Mosaic myofibers with donor (white arrows) and recipient (black arrows) nuclei.

The glucose phosphate isomerases (GPI) of the injected muscles were also examined with agarose gel electrophoresis (200 V anode to cathode, 3 hours, pH 8.6). The first appearance of mosaic myofibers in the tissue sections was within seven days after cell injection. This is illustrated in FIG. 7. The highest fusion rate achieved was 72.2%. The electrophoreograms of GPI showed host donor and mosaic GPI in muscle specimens at least up to 44 days after MTT. Myoblasts injected obliquely through the myofibers were widely and evenly distributed with ejection of the myoblasts as the needle is withdrawn. This is shown in FIG. 8. Myoblasts injected perpendicular to the myofibers were partially distributed, while myoblasts that were injected longitudinally through the core of the muscles and parallel to the myofibers were poorly distributed. Similarly, injection at one spot gave poor distribution and fusion. Considering that a small volume of a concentrated solution causes less muscle damage than a larger volume of a relatively less concentrated solution, and in view of the trauma caused by injection decreases the regenerative capability of dystrophic muscles, the technique of myoblast delivery is essential for MTT success.

Although oblique injection has been used in our clinical trials, there is room for improvement since human muscles are larger and the myofiber orientation of different muscle groups have to be well-studied by the orthopedic surgeons who administer myoblast injections. Judging from previous mouse studies, 20% normal myonuclei were able to maintain normal phenotype in dystrophic myofibers.

F. Exercise and Physical Therapy

Strenuous exercise causes damage to dystrophic myofibers. Lack of dystrophin causes the vulnerable sarcolemma to tear upon contraction. Other cell types are somewhat spared from degeneration because they do not contract. Thus, body building is counter-productive in DMD patients to compensate for loss of muscle mass and strength.

The use of exercise, however, in relation to MTT has not been studied. In dystrophic animals, it is well known that exercise hastens the degeneration of myofibers and thus aggravates the dystrophic condition, that is with dystrophic muscle fibers alone. The situation is different from MTT in which an attempt is made to produce a mosaic muscle containing normal, mosaic, and dystrophic fibers. The essence of MTT is to reconstruct the genetics and improve the phenotypes of dystrophic muscles. Thus, intensive exercise may induce the release of host satellite cells that will fuse with normal myoblasts to produce mosaic fibers. Undoubtedly, such dystrophic degeneration will induce normal muscle regeneration. Implanted myoblasts not only fuse to the newly sealed regions of damaged myofibers, but also survive as satellite cells. Mild exercise done shortly after MTT can be designed to facilitate myoblast mixing, alignment, and fusion, and to provide physical therapy to the newly formed fibers. Moderate exercise after innervation of newly formed fibers is likely to enhance the development of normal and mosaic fibers. Disuse plays a major role in the continued deterioration of dystrophic muscles, and physical therapy is prescribed for dystrophic patients. Disuse or lack of cross-bridge interaction results in a decrease of calcium binding. As a result, the excessive intracellular calcium promotes muscle damage in dystrophic muscles.

G. Myotube Transfer

In the later stages of DMD, there remains fewer myofibers to be repaired with MTT. Formation of new fibers to replenish degenerated cells is further complicated by the presence of excessive connective and fat tissues. While it takes approximately 1 to 3 weeks for donor myonuclei to be incorporated into dystrophic fibers for repair, it takes over 4 months for donor myoblasts to develop into mature normal fibers de novo to replenish lost cells. Meanwhile, the impediment to developing myotubes to be vascularized, innervated, and connected to tendons all threaten their survival. Enough nutrients have to be present for the developing fibers to lay down the contractile filaments myosin and actin. Neither electrical nor contractile activity is normal for the development of the fibers. This is the time when myotube transfer may be of help.

Transplants of newborn normal muscles or myotubes into $dy^{2J}/dy^{2J}$ dystrophic mouse muscles have been shown by this inventor to produce normal muscle function and structure. (See Law, P. K. and Yap, J. L., Muscle Nerve, 2:356–63 (1979)). Myotubes are easily obtained in culturo through natural myoblast fusion by exposing confluent cultures to the fusion medium. In fact, small muscles have been produced with spontaneously contracting fibers in culture. The young fibers exhibit sarcomeres and immunostain positively for myosin.

Myotube transfer can be administered through injection with larger gauge needles. Better still, they can be surgically implanted into the beds of fat and connective tissues dissected and removed by surgeons. Since muscles can develop great forces and scar tissues are inert, the developing muscles will force the scar tissues aside throughout their existence.

Myotube transfer provides bioengineered young fibers in vitro. These fibers have lost their MHC-I surface antigens and are thus nonantigenic. Myotube transfer will not need to be administered with cyclosporin. For patients previously infected with cytomegalovirus (CMV) or other viruses, myotube transfer will be the choice.

In addition, for autosomal dominant diseases such as facioscapulohumeral dystrophy (FSH), myotonia congenita, myotonia dystrophica and certain forms of congenital muscular dystrophy and limb-girdle dystrophy, formation of mosaic fibers may not be useful since nuclear complementation may not be effective. The use of entirely normal myotubes through myotube transfer will undoubtedly open new avenues for treatment.

H. Allophenic Mice

Allophenic mice or mouse chimaeras are mice mosaics with two or more genotypes. They are produced by blastomere recombination (see Hogan B., et al. Manipulating the Mouse Embryo. A Laboratory Manual. Cold Spring Harbor Laboratory, (1986)) or by the artificial aggregation of embryos from two different strains of mice. In addition to being important specimens to study the clonal origins of somites and their muscle derivatives, allophenic mice have been shown by this inventor and others to demonstrate dystrophy suppression in natural development when genetically normal and dystrophic myogenesis coexist.

Figure 9:
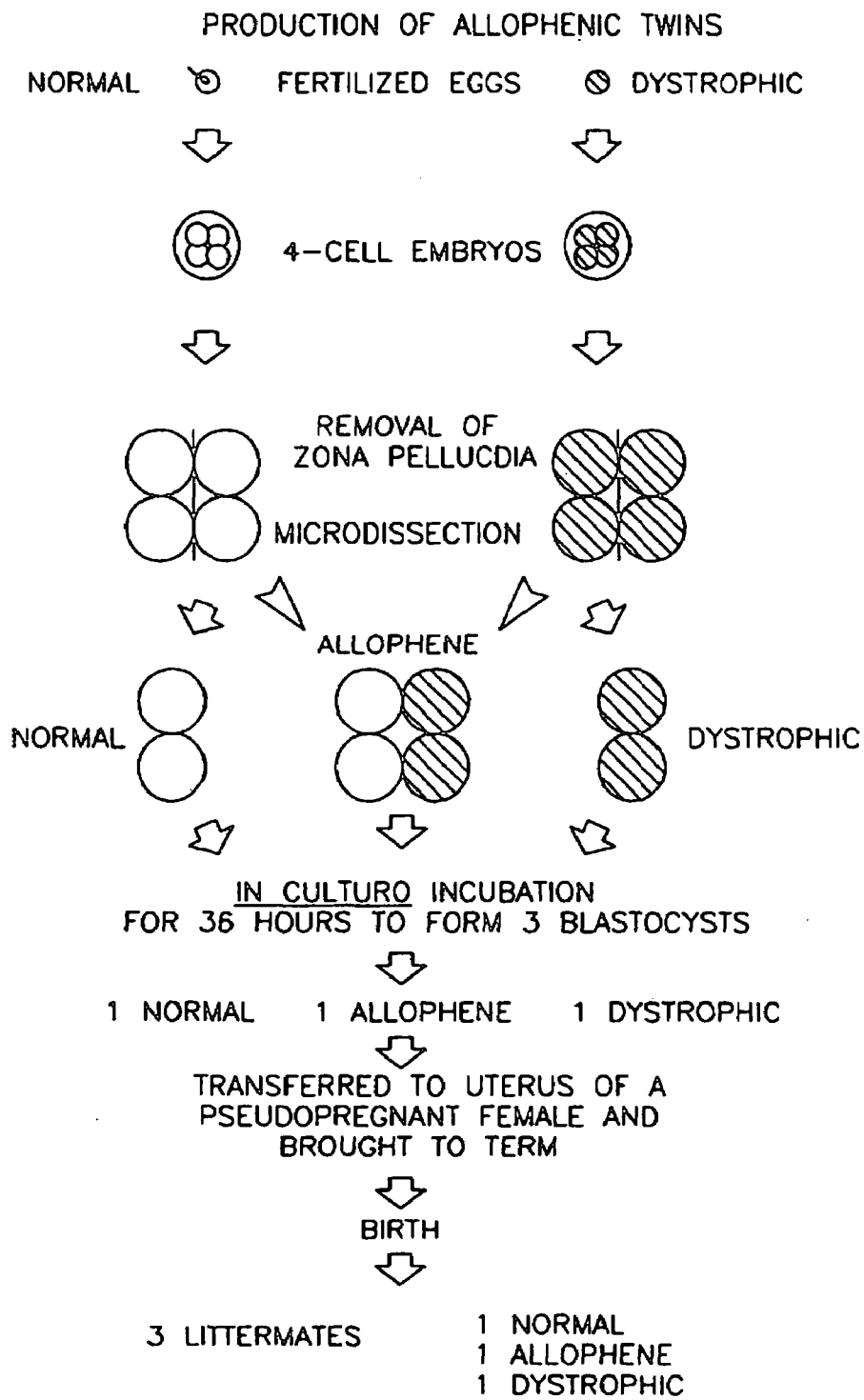
FIG. 9 illustrates the production of allophenic twins with the mechanism of allophene formation.
Figure 10:
FIG. 10 illustrates three littermates: 1 normal, 1 allophene, 1 dystrophic (top to bottom).
Figure 11:
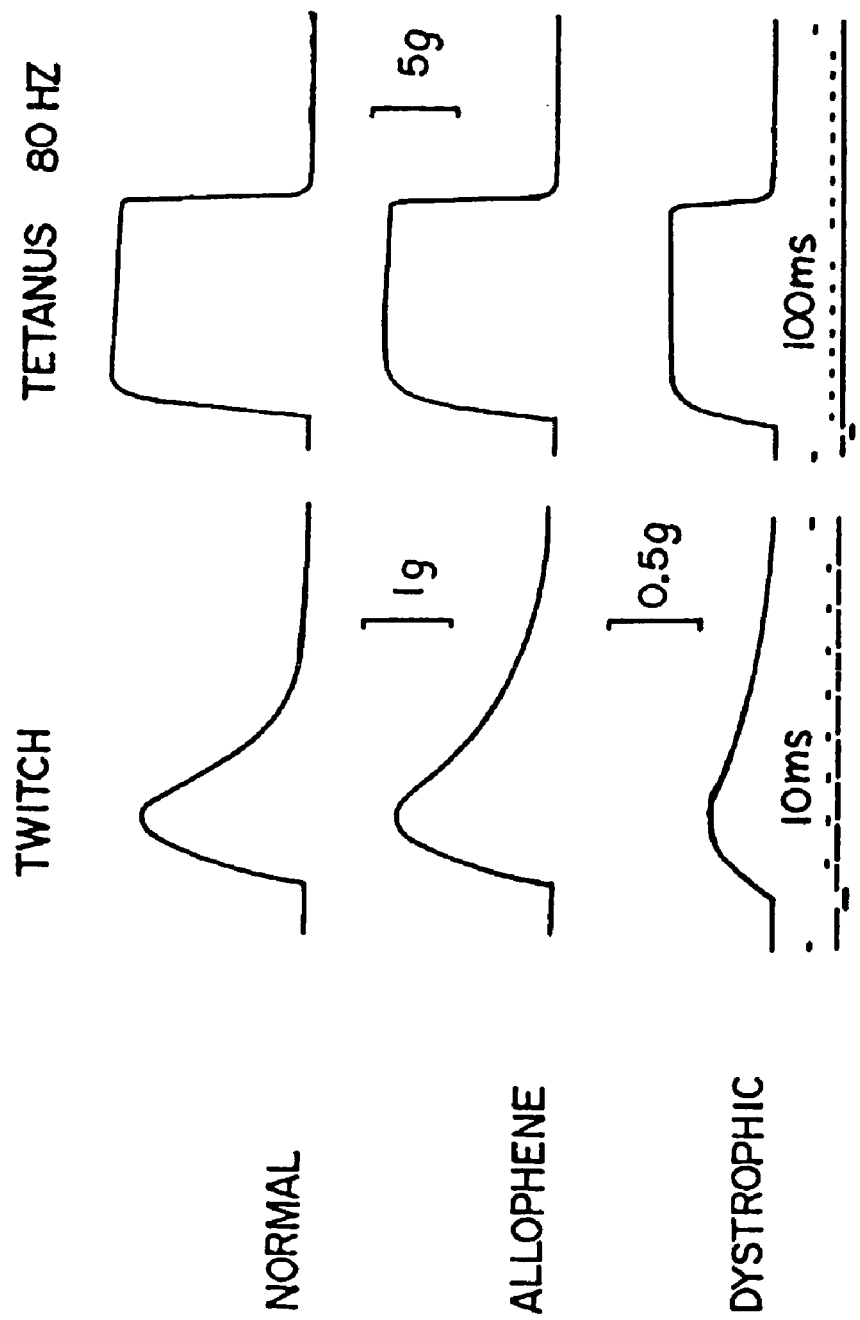
FIG. 11 illustrates physiological recordings of maximal isometric twitch and tetanus tensions at 80 Hz elicited from the soleus muscles of the normal, allophenic, and dystrophic littermates. The allophene recordings resemble the normal, rather than the dystrophic recordings.
Figure 12:
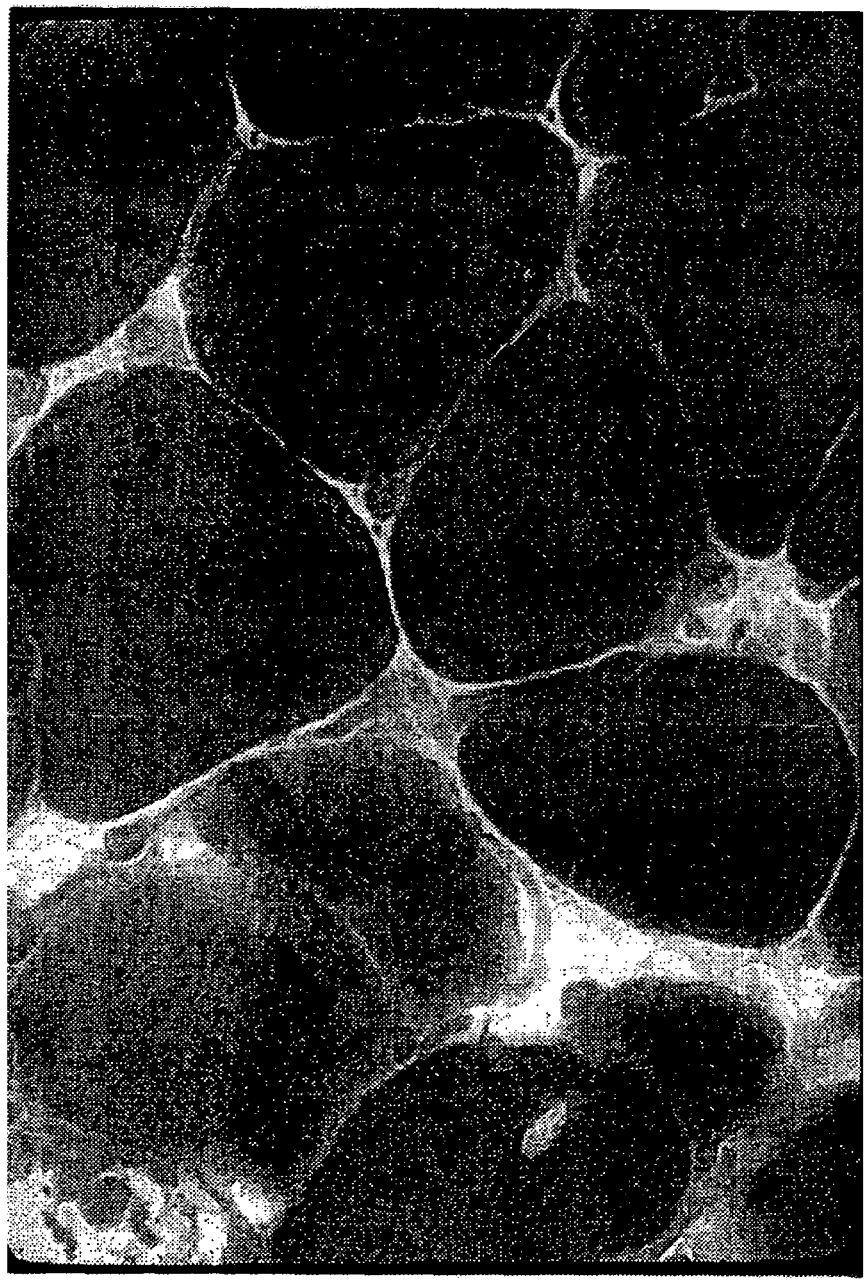
FIG. 12 illustrates soleus cross-sections from allophenic mice demonstrating core fibers (arrows) characteristic of muscle from DMD carriers. Whereas most myofibers remain normal in appearance, some degenerative characteristics such as fiber splitting and central nucleation are apparent.
Figure 13:
FIG. 13 further illustrates soleus cross-sections from allophenic mice demonstrating core fibers (arrows) characteristic of muscle from DMD carriers. Although most myofibers remain normal in appearance, some degenerative characteristics are visible such as fiber splitting and central nucleation.

By aggregating half embryos of normal (129 strain) and dystrophic (C57BL/6J $dy^{2J}/dy^{2J}$ strain) mice as shown in the diagram of FIG. 9, sets of allophenic twins were produced consisting of chimaeric mice and their normal and dystrophic littermates (FIG. 10). Although the dystrophic gene was present in the muscle fibers according to genotype marker analyses, these allophenic mice showed normal behavior, life span, and essentially normal muscle function shown in FIG. 11 and structure in FIGS. 12 and 13.

Muscle fibers of these allophenic mice highly resemble those of the Duchenne female carriers. Whereas the dystrophic soleus contains 70% or more degenerating fibers, only 3 to 5% of the allophenic soleus fibers are abnormal. Many of these abnormal fibers showed "cores" as seen in the Duchenne carriers. Through natural cell fusion, normal myoblasts fuse with dystrophic ones to form mosaic myotubes that develop into phenotypically normal fibers.

I. Normal Child for a Duchenne Carrier

Conceivably the technology of in vitro fertilization and blastomere recombination used in the allophenic mouse studies can be applied to human. Known carriers may thus have better chances of bearing normal children.

Accordingly, ova from a carrier and from a normal female can be obtained and fertilized in vitro with sperm recovered from the carrier's husband. The fertilized egg of the carrier has a 50/50 chance of being normal or dystrophic. Regardless of its genotype, its mixing with the normal fertilized egg will ensure the development of a normal phenotype. After culturing the embryo into the blastocyst stage, it can be implanted into the uterus of the carrier. The latter can be induced to be pseudo-pregnant with human gonadotrophin, thus allowing easy implantation.

The use of in vitro fertilization protects the mother. Abnormal developing embryos after blastomere recombination can be discarded. Furthermore, no blastomere needs to be removed for genetic analysis.

Since the fertilized egg of the carrier has 50% chance of being normal, a PCR analysis for dystrophin messenger RNA can be conducted on blastomeres removed from the embryo at the blastocyst stage. Unfortunately, this risks damaging the embryo by removing part of it at an early developmental stage.

J. Automated Cell Processors

With the great demand for normal myoblasts, myotubes and young muscles, the labor intensiveness and high cost of cell culturing, harvesting and packaging, and the fallibility of human imprecision, an automated cell processor is needed. Such a processor would be capable of producing mass quantities, over 100 billion per run, of viable, sterile, genetically well-defined and functionally demonstrated biologics, for example, myogenic cells.

Figure 14:
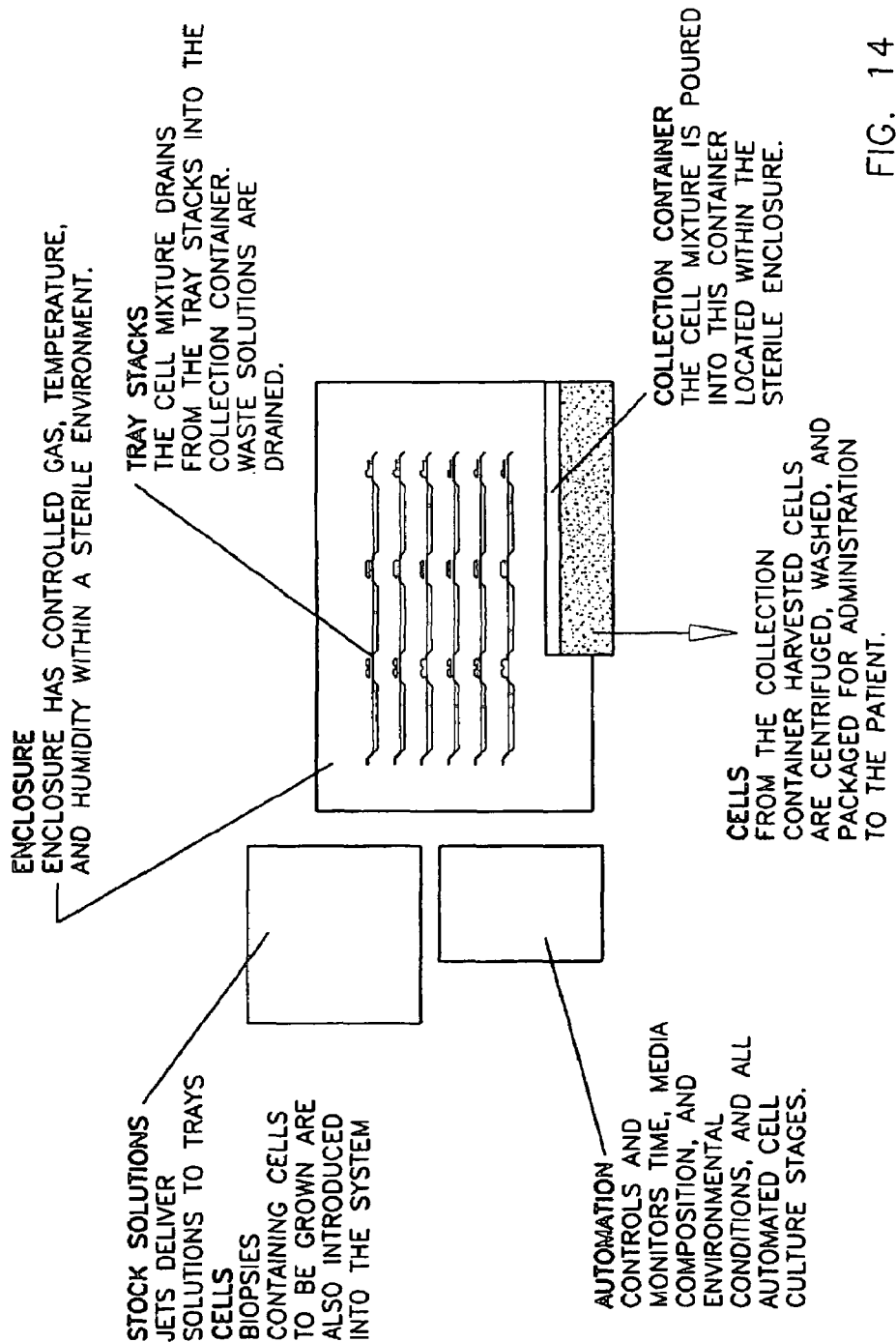
FIG. 14 illustrates the general layout of an automated cell processor.
Figure 15A:
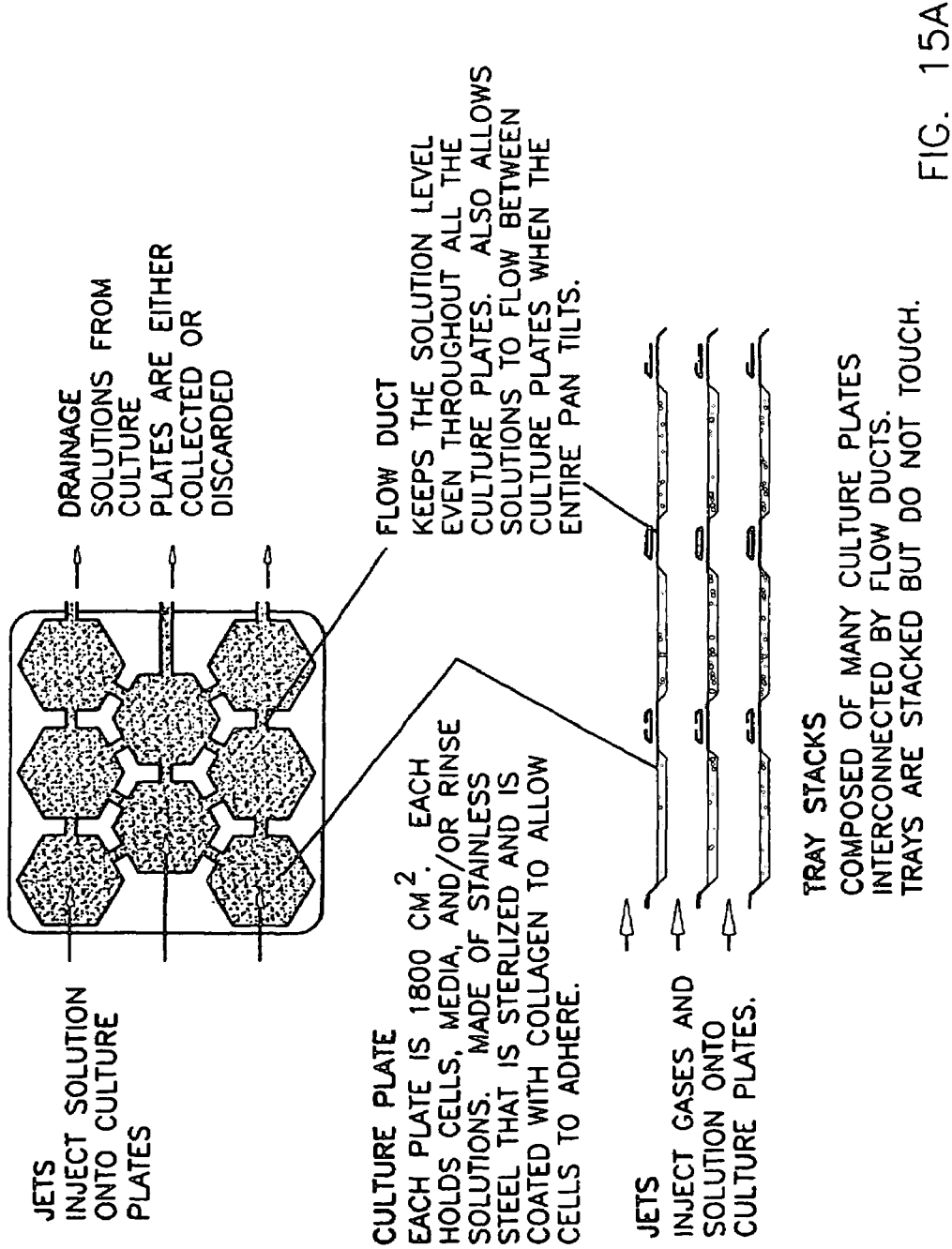
FIG. 15 illustrates the detailed design of culture and harvest automated actions.
Figure 15B:
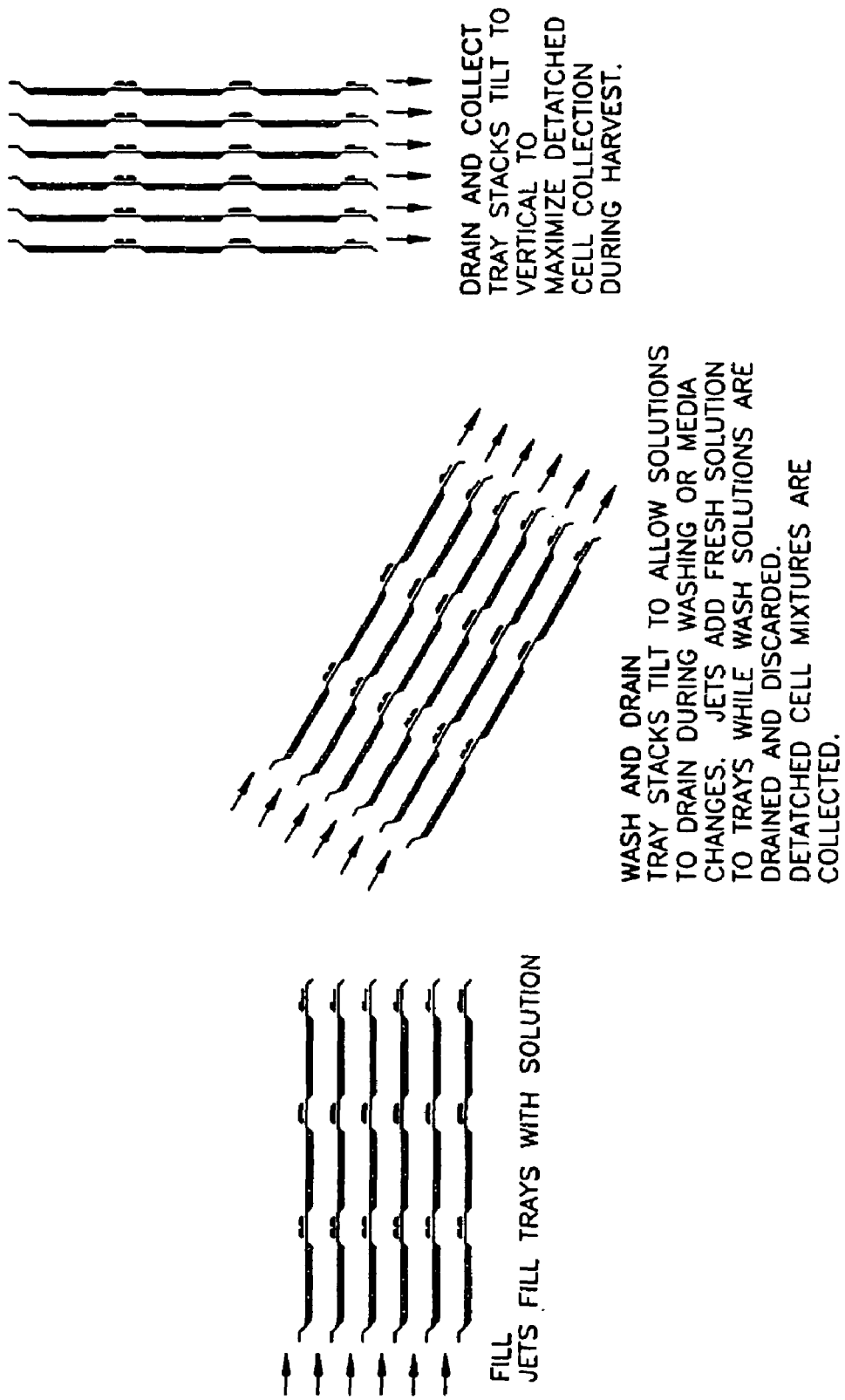
Figure 16A:
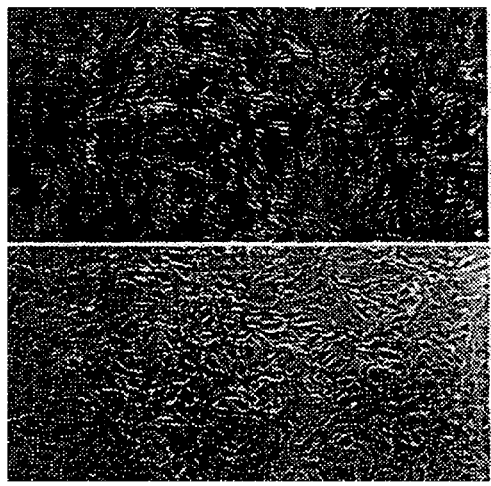
FIG. 16 is a comparison of cancer cell growth media with myoblast growth media on cultured melanoma (CRL6322) cells. (A, C, E, G) low magnification; (B, D, F, H) high magnification. (A, B) Melanoma cells cultured in cancer cell growth media for 9 days appear healthy, as evidenced by their numbers, elongated shapes, and branching processes. (C, D) Similar amount of melanoma cells seeded and cultured in myoblast growth media for 9 days are more numerous and differentiated. (E, F) After 14 days in cancer cell growth media, the melanoma cells, while numerous, have become spherical in shape and detached from the surface, indicating that the cells are dead (E). At higher magnification only a few healthy cells remain (F). (G, H) After 14 days in myoblast growth media, the melanoma cells still appear numerous and healthy.
Figure 16B:
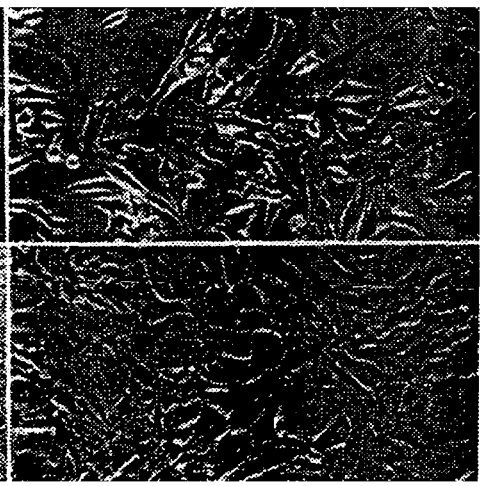
Figure 16C:
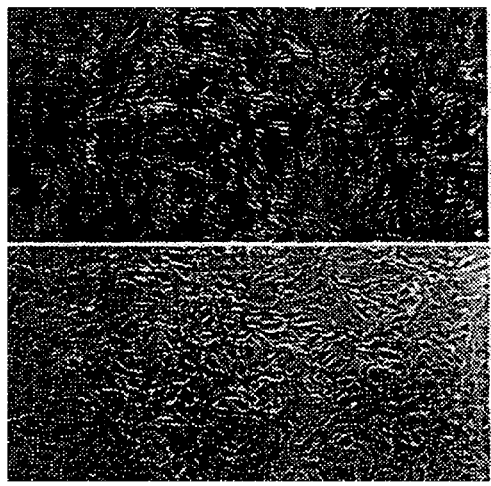
Figure 16D:
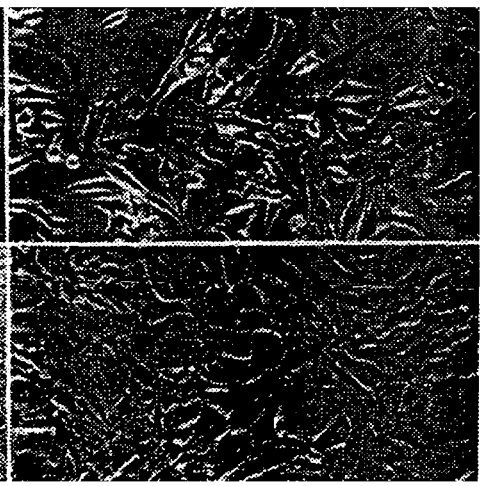
Figure 17A:
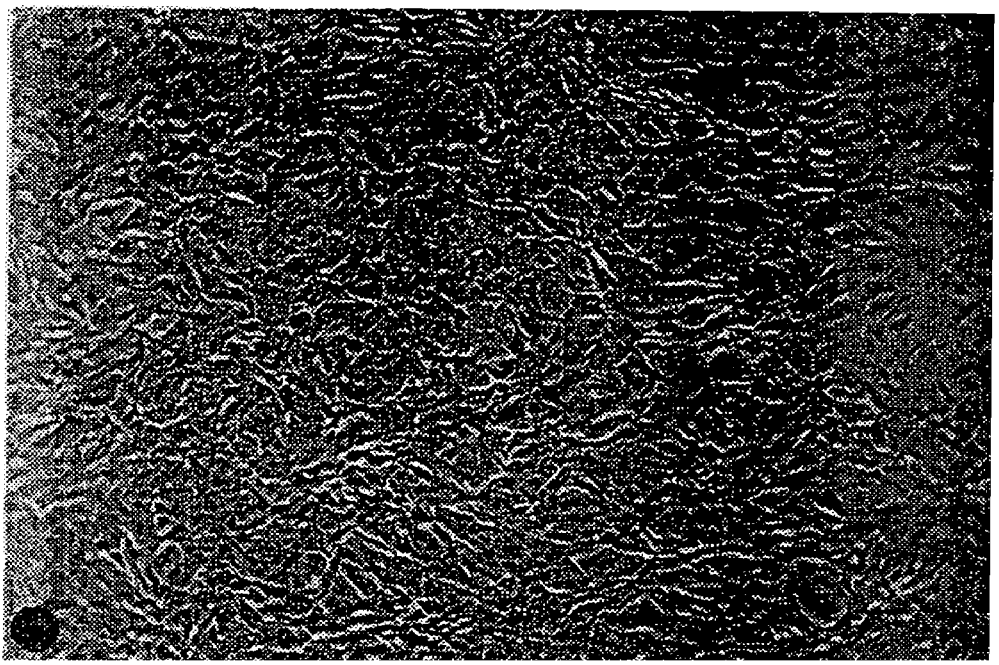
FIG. 17 illustrates myoblasts and melanoma cells (2:1 concentration ratio) co-cultured in myoblast growth media. (A, C) low magnification; (B, D) high magnification. (A, B) After 9 days in culture myoblasts and melanoma cells are numerous and remain is differentiated. (C, D) After 14 days in culture myoblasts dominate the culture, with melanoma cells still surviving.
Figure 17B:
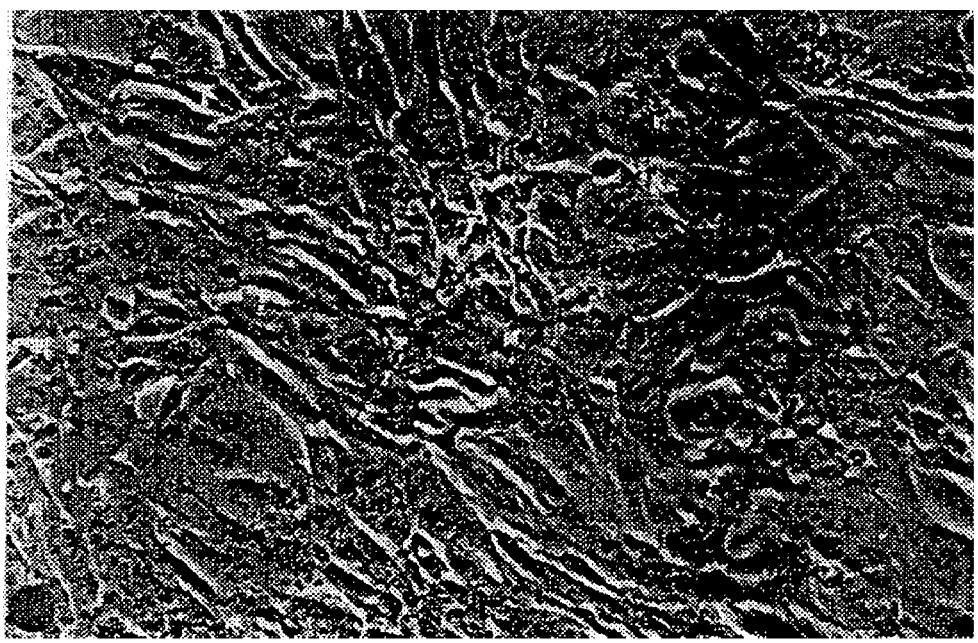
Figure 17C:
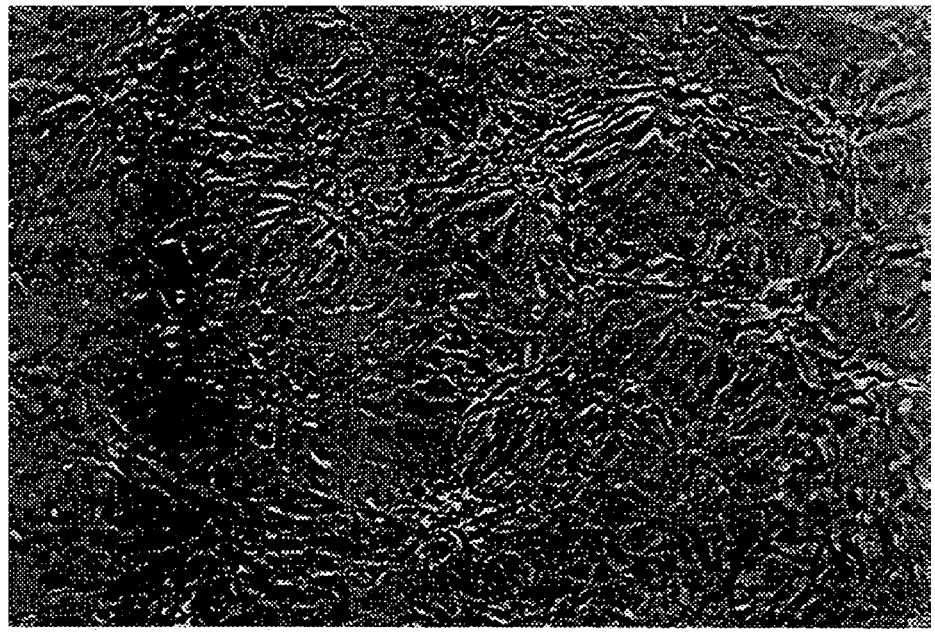
Figure 17D:
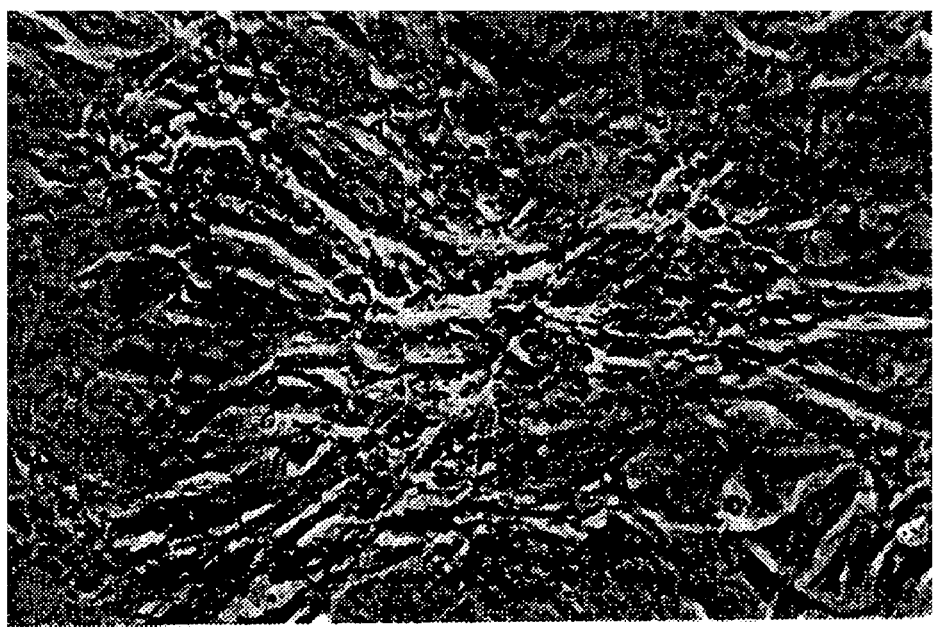
Figure 19A:
FIG. 19 is an immunocytochemical demonstration of dystrophin in human muscle. Sarcolemmal localization of dystrophin is shown in normal control muscle (A) but not in DMD muscle (B). (C, D) DMD biceps brachii muscles from a subject who received MTT in one biceps and placebo injections in the contralateral muscle 9 mo before biopsies. Since blinding continues until the end of the study, the designation of the MTT muscle cannot be revealed. However, only one muscle shows sarcolemmal localization of dystrophin. (B), (C), and (D) were intentionally over-exposed to show immuno-reactive background elements not associated with the sarcolemma.
Figure 19B:
Figure 19C:
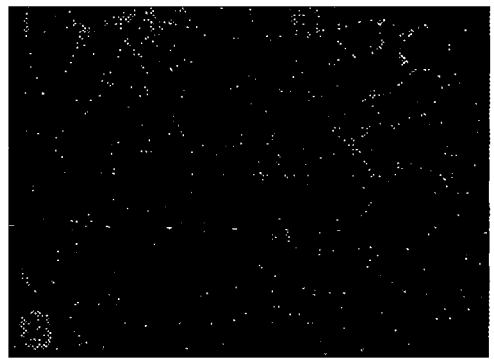
Figure 19D:
Figure 20A:
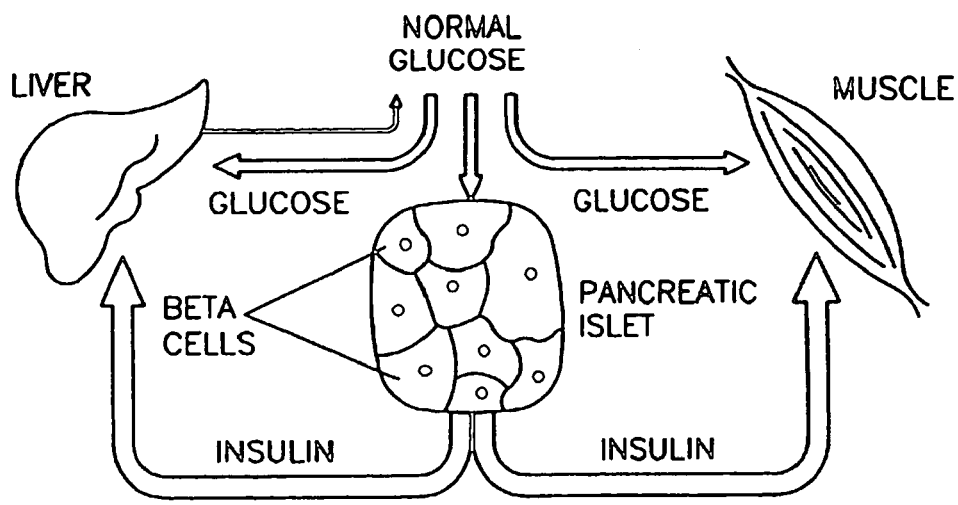
FIG. 20 illustrates (a) normal skeletal muscle metabolizing glucose with insulin. (b), (c) In Type II diabetes mellitus, the major sequela of insulin resistance is decreased muscle uptake of glucose both in response to meals (20 b) and during fasting (20c). It is possible that the glucose transporter in muscle is abnormal. It is known that insulin-mediated stimulation of tyrosine kinase and autophosporylation are impaired. These latter defects can be corrected by MTT by normal gene expression (from Metabolism 6:6, 1993).
Figure 20B:
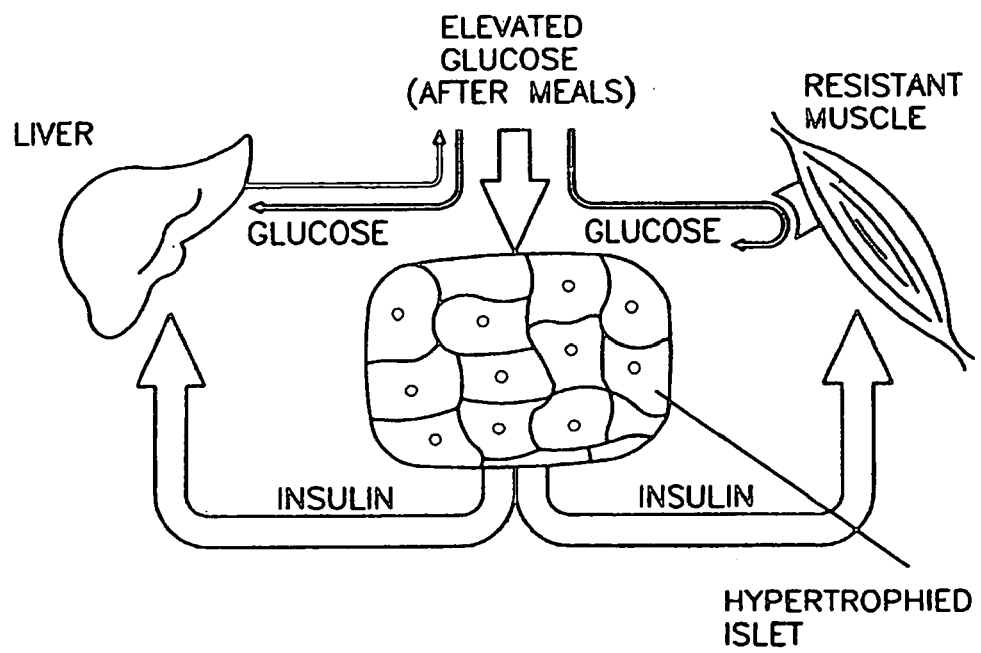
Figure 20C:
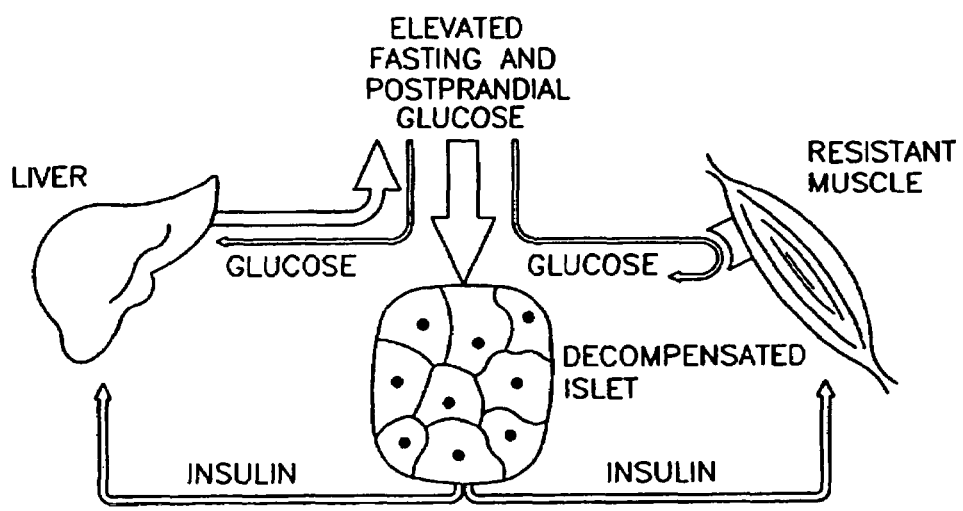

The automated cell processor will be one of the most important offspring of modern day computer science, mechanical engineering and cytogenetics (FIG. 14). The intakes will be for the biopsies of various human tissues. The computer will be programmed to process tissue(s), with precision control in time, space, and proportions of culture ingredients and apparatus maneuvers. Cell conditions can be monitored at any time during the process, and flexibility is built-in to allow changes. Different protocols can be programmed into the software for culturing, controlled cell fusion, harvesting and packaging. The outputs will supply cells, which will be ready for shipment or for injection using cell therapy. The automated cell processor will be self-contained in a sterile enclosure large enough to house the hardware in which cells are cultured and manipulated (FIG. 15).

This inventor has developed a transfer medium that can sustain the survival and myogenicity of packaged myoblasts for up to 3 days at room temperature. Survival up to 7 days can be achieved when the myoblasts are refrigerated. This will allow the cell packages to be delivered to remote points of utilization around the world.

The automated cell processor will simply replace current bulky inefficient culture equipment and elaborate manpower. Its contribution to human healthcare will undoubtedly be significant, and the manufacturing costs are expected to be relatively low.

K. Cell Banks

The automated cell processors will constitute only a part of cell banks. Ideally, donor muscle biopsies can be obtained from young adults aged 8 to 22 to feed the inputs of the automated cell processor. This will depend on the availability of healthy volunteer donors. Each donor has to undergo a battery of tests that are time-consuming and expensive. Based on the test results and the donor's physical condition, one can determine if the donor cells are genetically defective or infected with viruses and/or bacteria. These are the advantages of biopsies of mature tissues from adults. The major disadvantage, however, is that mature cells often do not divide, and even if they do, there is a limited number of generations that can propagate before becoming tumorigenic or nonmitotic.

Human fetal tissues can potentially provide unlimited supplies of dividing cells. However, aside from ethical issues, it is difficult to determine the genetic normality of these cells, notwithstanding the existence of polymerase chain reaction (PCR) which is used to screen many human genetic diseases.

As for the muscular dystrophies, the use of muscle primordia of fetal calves derived from in vitro fertilization of genetically well-defined background may be an alternative. Sperms and ova can be recovered from inbred strains of cattles that are known for their muscle strength and mass. In vitro fertilization will be followed by embryo culture and implantation into the uteruses of pseudo-pregnant cows. The fetuses are removed by Sicilian sections at specific developmental stages of the embryos. The muscle primordia that are rich in myoblasts can then be dissected out to feed into the automated cell processors.

Transplantation of cattle cells into humans constitutes xenografting. Due to the significant differences between the human and the cattle immune systems, these xenografts will likely survive, develop and function in the recipients without the need for immunosuppressants. However, the method will be tested with and without immunosuppressants.

L. Myoblast Derivatives vs. Cancer

Evolution is one continual experiment through ages with numerous statistics. The near absence of cancer metastases in skeletal muscles suggests that the physical, electrical, mechanical or chemical presence of myogenic cells and derivatives prevents or annihilates cancer.

In our study we showed that the physical and biochemical conditions of myoblast at the cell fusion stage caused the death of melanoma cancer cells (FIG. 16 to 18). This does not preclude the potential effect of similar or different conditions, including electrical and mechanical, of other myogenic cells at different developmental stages.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for treating a body part of a subject, comprising (a) culturing myogenic cells to form a composition of cells and then (b) administering said composition into the body part such that the cosmetic appearance of the subject is altered.

2. A method as described in claim 1, wherein said body part is a face, breast, hip or non-diseased muscle.

3. A method as described in claim 1, wherein said myogenic cells are administered by injection into said body part.

4. A method as described in claim 1, wherein said myogenic cells are MHC-1 antigen deficient.

5. A method as described in claim 4, wherein said MHC-1 antigen deficient cells are produced by:
   (a) tagging MHC-1 antigen deficient cells in a cell population by fluorescent immunoassay;
   (b) removing the tagged cells; and
   (c) proliferating the removed cells.

6. A method as described in claim 1, wherein said composition further comprises fat cells.

7. A method as described in claim 1, further comprising administering chondroitin sulfate into the body part, together with or separately from the administration of myogenic cells into the body part.

8. In a method for augmenting a body part with plastic surgery of the body part by implantation of silicone, the improvement consisting of replacing injection of silicone with multiple transverse injection of a composition that comprises myogenic cells.

9. A method as described in claim 8, wherein the composition further comprises added chondroitin sulfate in a concentration between 5 uM and 5 mM.

10. A method as described in claim 8, wherein the body part is a face, breast, hip, or non-diseased muscle.

11. A method for augmenting a body part comprising:
   (a) dissecting and removing tissue from the body part; and
   (b) surgically implanting myotubes into the body part.

12. A method as described in claim 11, wherein the tissue is fat and/or connective tissue.

* * * * *